(12) United States Patent
Elias et al.

(10) Patent No.: US 12,312,411 B2
(45) Date of Patent: *May 27, 2025

(54) ANTI-CD38 BINDING DOMAINS

(71) Applicant: Takeda Pharmaceutical Company Limited, Osaka (JP)

(72) Inventors: Kathleen Ann Elias, San Francisco, CA (US); Gregory Landes, San Bruno, CA (US); Shweta Singh, South San Francisco, CA (US); Wouter Korver, South San Francisco, CA (US); Andrew Walling Drake, South San Francisco, CA (US); Mary Haak-Frendscho, San Francisco, CA (US); Vinay Bhaskar, San Francisco, CA (US); Erin Willert, Round Rock, TX (US)

(73) Assignee: Takeda Pharmaceutical Company Limited, Osaka (JP)

(*) Notice: Subject to any disclaimer, the term of this patent is extended or adjusted under 35 U.S.C. 154(b) by 269 days.

This patent is subject to a terminal disclaimer.

(21) Appl. No.: 17/810,377

(22) Filed: Jul. 1, 2022

(65) Prior Publication Data

US 2023/0203186 A1 Jun. 29, 2023

Related U.S. Application Data

(63) Continuation of application No. 16/751,107, filed on Jan. 23, 2020, now Pat. No. 11,414,496.

(60) Provisional application No. 62/795,855, filed on Jan. 23, 2019.

(51) Int. Cl.
*A61K 39/395* (2006.01)
*C07K 16/28* (2006.01)

(52) U.S. Cl.
CPC ...... *C07K 16/2896* (2013.01); *C07K 2317/33* (2013.01); *C07K 2317/565* (2013.01); *C07K 2317/622* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,887,801 B2 | 2/2011 | Weis et al. | |
| 8,530,637 B2 | 9/2013 | Weis et al. | |
| 9,603,927 B2* | 3/2017 | Doshi | A61P 35/00 |
| 10,815,469 B2 | 10/2020 | Poma et al. | |
| 11,414,496 B2 | 8/2022 | Elias et al. | |
| 11,713,347 B2 | 8/2023 | Chattopadhyay et al. | |
| 2015/0259428 A1 | 9/2015 | Poma et al. | |
| 2016/0068577 A1 | 3/2016 | Poma et al. | |
| 2016/0177284 A1 | 6/2016 | Poma et al. | |
| 2016/0340394 A1 | 11/2016 | Poma et al. | |
| 2016/0347798 A1 | 12/2016 | Poma et al. | |
| 2016/0376328 A1 | 12/2016 | Poma et al. | |
| 2017/0143814 A1 | 5/2017 | Poma et al. | |
| 2018/0258143 A1 | 9/2018 | Poma et al. | |
| 2020/0231650 A1 | 7/2020 | Chattopadhyay et al. | |
| 2020/0231696 A1 | 7/2020 | Elias et al. | |
| 2022/0275030 A1 | 9/2022 | Poma et al. | |

FOREIGN PATENT DOCUMENTS

| | | |
|---|---|---|
| CN | 103282383 A | 9/2013 |
| CN | 105473615 A | 4/2016 |
| CN | 106414503 A | 2/2017 |
| CN | 107849096 A | 3/2018 |
| JP | 2014-509187 A | 4/2014 |
| JP | 2016-522816 A | 8/2016 |
| WO | WO 98/11125 A1 | 3/1998 |
| WO | WO 2012/092612 A1 | 7/2012 |
| WO | WO 2012/092616 A1 | 7/2012 |
| WO | WO 2014/164680 A1 | 10/2014 |
| WO | WO 2014/164693 A2 | 10/2014 |
| WO | WO 2014/178820 A1 | 11/2014 |
| WO | WO 2015/113005 A1 | 7/2015 |
| WO | WO 2015/113007 A1 | 7/2015 |
| WO | WO 2015/138435 A1 | 9/2015 |
| WO | WO 2015/138452 A1 | 9/2015 |
| WO | WO 2015/191764 A1 | 12/2015 |
| WO | WO 2016/126950 A1 | 8/2016 |
| WO | WO 2016/196344 A1 | 12/2016 |
| WO | WO 2017/019623 A2 | 2/2017 |
| WO | WO 2018/083126 A1 | 5/2018 |
| WO | WO 2018/106895 A1 | 6/2018 |
| WO | WO 2018/140427 A1 | 8/2018 |
| WO | WO 2018/159615 A1 | 9/2018 |

(Continued)

OTHER PUBLICATIONS

U.S. Appl. No. 16/751,144, filed Jan. 23, 2020, Chattopadhyay et al.
International Search Report and Written Opinion for Application No. PCT/US2020/014845 mailed May 25, 2020.
International Preliminary Report on Patentability for Application No. PCT/US2020/014845 mailed Aug. 5, 2021.
No Author Listed, Darzalex, Annex I: Summary of Product Characteristics. European Medicines Agency. 2016. 46 pages.

(Continued)

*Primary Examiner* — Meera Natarajan

(74) *Attorney, Agent, or Firm* — Wolf, Greenfield & Sacks, P.C.

(57) ABSTRACT

Provided in this disclosure are anti-CD38 binding domains, a composition comprising the anti-CD38 binding domains, nucleic acids encoding the anti-CD38 binding domains, and a method of using the anti-CD38 binding domains or the composition for treating multiple myeloma.

20 Claims, 21 Drawing Sheets

Specification includes a Sequence Listing.

(56) References Cited

FOREIGN PATENT DOCUMENTS

WO    WO 2020/154531 A1    7/2020
WO    WO 2020/154540 A1    7/2020

OTHER PUBLICATIONS

No Author Listed, CD38 recombinant monoclonal antibody, clone HB7. Abnova Datasheet. Catalog # : RAB00097. 1 page. Last accessed: Mar. 15, 2023. http://www.abnova.com/products/products_detail.com.

* cited by examiner

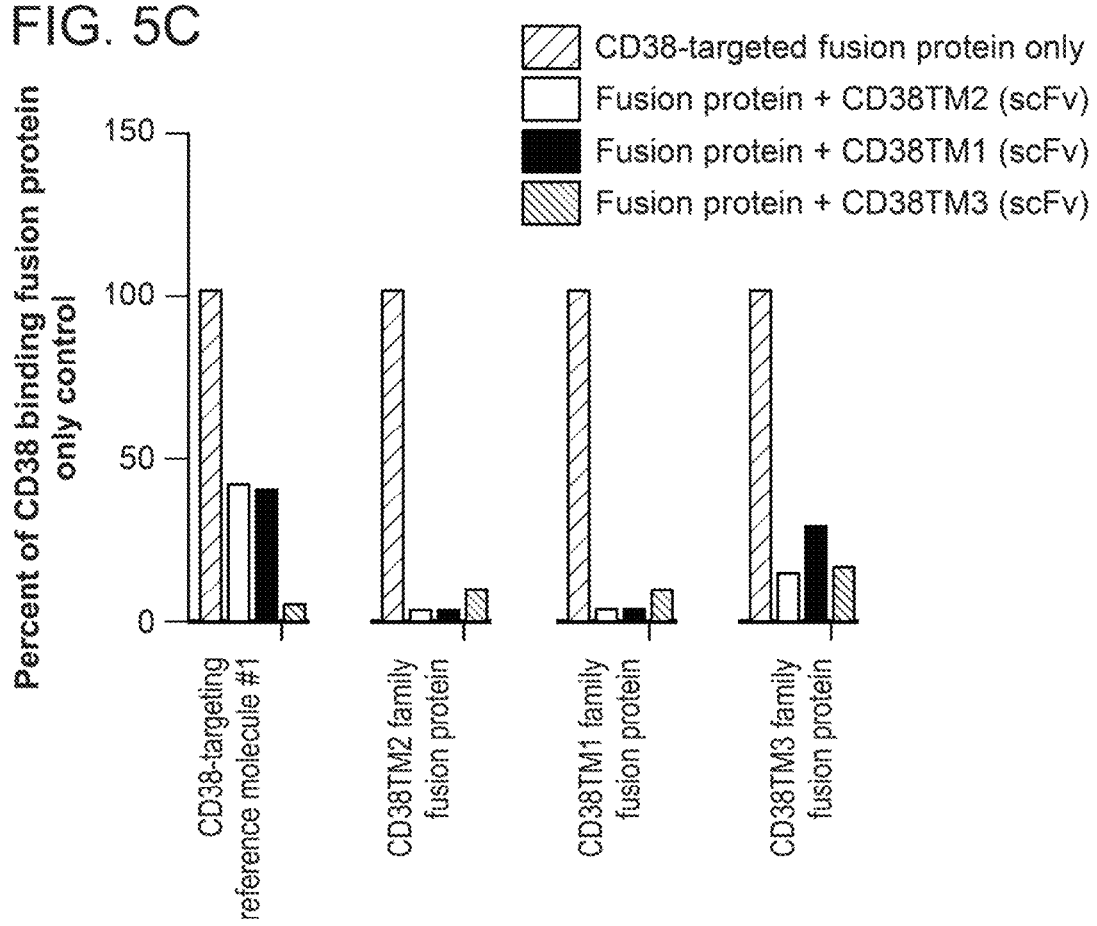

FIG. 6A

CD38-Targeting Moiety #3 (CD38TM3)

| What | sequence | SEQ ID NO: |
|---|---|---|
| VH domain | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARGPSTGFWSGNYFDYWGQGTLVTVSS | 1 |
| vhCDR1 | GYSFTSYW | 2 |
| vhCDR2 | IYPGDSDT | 3 |
| vhCDR3 | ARGPSTGFWSGNYFDY | 4 |
| VL domain | QTVVTQEPSLTVSPGETVTLTCASSTGAVTSGFYPNWFQQKPGQAPRALIYATNNKYSWTPARFSGSLLGDKAALTLSRVQPEDEADYYCLVYYDGAWVFGGGTKLTVLG | 5 |
| vlCDR1 | TGAVTSGFY | 6 |
| vlCDR2 | ATN | 7 |
| vlCDR3 | LVYYDGAW | 8 |

FIG. 6B
CD38-Targeting Moiety #1 (CD38TM1)

| What | sequence | SEQ ID NO: |
|---|---|---|
| VH domain | EVQLLESGGGLVQPGGSLRLSCAASGFTFSDYYMSWVRQAPGKGLEWVSAISGSGGSTYYADSVKGRFTISRDNSKNTLYLQMNSLRAEDTAVYYCAREHSNYFYGMDVWGQGTLVTVSS | 9 |
| vhCDR1 | GFTFSDYY | 10 |
| vhCDR2 | ISGSGGST | 11 |
| vhCDR3 | AREHSNYFYGMDV | 12 |
| VL domain | QSVLTQPPSASGTPGQRVTISCSGSSSNIGSNYVYWYQQLPGTAPKLLIYGNSNRPSGVPDRFSGSKSGTSASLAISGLRSEDEADYYCQSYDSSLSGSGVFGGGTKLTVLG | 13 |
| vlCDR1 | SSNIGSNY | 14 |
| vlCDR2 | GNS | 15 |
| vlCDR3 | QSYDSSLSGSG | 16 |

FIG. 6C
CD38-Targeting Moiety #2 (CD38TM2)

| What | sequence | SEQ ID NO: |
|---|---|---|
| VH domain | EVQLLESGGGLVQPGGSLRLSCAASGFTFSSYWMHWVRQAPGKGLEWVSAISGSGGGTFYADSVKGRFTISRDNSKNTLYLQMNSLRAEDTAVYYCAREGETSFGLDVWGQGTLVTVSS | 17 |
| vhCDR1 | GFTFSSYW | 18 |
| vhCDR2 | ISGSGGGT | 19 |
| vhCDR3 | AREGETSFGLDV | 20 |
| VL domain | QSVLTQPPSASGTPGQRVTISCSGSSSNIGGNYVYWYQQLPGTAPKLLIYRNNQRPSGVPDRFSGSKSGTSASLAISGLRSEDEADYYCQSYDSSLSVSVFGGGTKLTVLG | 21 |
| vlCDR1 | SSNIGGNY | 22 |
| vlCDR2 | RNN | 23 |
| vlCDR3 | QSYDSSLSVS | 24 |

FIG. 6D
CD38-Targeting Moiety #4 (CD38TM4)

| What | sequence | SEQ ID NO: |
|---|---|---|
| VH domain | QVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARGPSTGFWSGNYFDYWGQGTLVTVSS | 1 |
| vhCDR1 | GYSFTSYW | 2 |
| vhCDR2 | IYPGDSDT | 3 |
| vhCDR3 | ARGPSTGFWSGNYFDY | 4 |
| VL domain | DIQMTQSPSSLSASVGDRVTITCASSTGAVTSGFYPNWFQQKPGQAPRALIYATNNKYSWTPARFSGSLLGDKAALTLSRVQPEDEADYYCLVYYDGAWVFGGGTKLTVLG | 25 |
| vlCDR1 | TGAVTSGFY | 6 |
| vlCDR2 | ATN | 7 |
| vlCDR3 | LVYYDGAW | 8 |

FIG. 6E
CD38-Targeting reference molecule #1 (CD38TR1)

| What | sequence | SEQ ID NO: |
|---|---|---|
| VH domain | QVQLQESGPGLVRPSQTLSLTCTVSGFSLTSYGVHWVRQPPGRGLEWIGVMWRGGSTDYNAAFMSRLNITKDNSKNQVSLRLSSVTAADTAVYYCAKSMITTGFVMDSWGQGSLVTVSS | 26 |
| VL domain | DIQMTQSPSSLSASVGDRVTITCKASEDIYNRLTWYQQKPGKAPKLLISGATSLETGVPSRFSGSGSGTDFTFTISSLQPEDIATYYCQQYWSNPYTFGQGTKVEIK | 27 |

FIG. 6F

CD38-Targeting Moiety #5 (CD38TM5)

| What | sequence | SEQ ID NO: |
|---|---|---|
| VH domain | EVQLLESGGGLVQPGGSLRLSCAASGFTFSDYYMNWIRQAPGKGLEWVSSISSSSSYIYYADSVKGRFTISRDNSKNTLYLQMNSLRAEDTAVYYCATEGPYYLYGFDIWGQGTLVTVSS | 53 |
| vhCDR1 | GFTFSDYY | 54 |
| vhCDR2 | ISSSSSYI | 55 |
| vhCDR3 | ATEGPYYLYGFDI | 56 |
| VL domain | QSVLTQPPSASGTPGQRVTISCSGSSSNIGSNYVYWYQQLPGTAPKLLIYGNSNRPSGVPDRFSGSKSGTSASLAISGLRSEDEADYYCQSYDNTLSGVIFGGGTKLTVLG | 57 |
| vlCDR1 | SSNIGSNY | 58 |
| vlCDR2 | GNS | 59 |
| vlCDR3 | QSYDNTLSGV | 60 |

FIG. 6G

CD38-Targeting Moiety #6 (CD38TM6)

| What | sequence | SEQ ID NO: |
|---|---|---|
| VH domain | EVQLLESGGGLVQPGGSLRLSCAASGFTFDDYGMTWVRQAPGKGLEWVSGINWNGGSTGYADSVKGRFTISRDNSKNTLYLQMNSLRAEDTAVYYCARGGLFHDSSGYYFGHWGQGTLVTVSS | 61 |
| vhCDR1 | GFTFDDYG | 62 |
| vhCDR2 | INWNGGST | 63 |
| vhCDR3 | ARGGLFHDSSGYYFGH | 64 |
| VL domain | QSVLTQPPSASGTPGQRVTISCSGSSSNIGNSYVSWYQQLPGTAPKLLIYRNNQRPSGVPDRFSGSKSGTSASLAISGLRSEDEADYYCSAWDDNLSVLFGGGTKLTVLG | 65 |
| vlCDR1 | SSNIGNSY | 66 |
| vlCDR2 | RNN | 67 |
| vlCDR3 | SAWDDNLSV | 68 |

FIG. 7

| What | Protein sequence | SEQ ID NO: |
|---|---|---|
| CD38 Homo sapiens | MANCEFSPVSGDKPCCRLSRRAQLCLGVSILVLILVVV LAVVVPRWRQQWSGPGTTKRFPETVLARCVKYTEIHP EMRHVDCQSVWDAFKGAFISKHPCNITEEDYQPLMKL GTQTVPCNKILLWSRIKDLAHQFTQVQRDMFTLEDTLL GYLADDLTWCGEFNTSKINYQSCPDWRKDCSNNPVSV FWKTVSRRFAEAACDVVHVMLNGSRSKIFDKNSTFGS VEVHNLQPEKVQTLEAWVIHGGREDSRDLCQDPTIKE LESIISKRNIQFSCKNIYRPDKFLQCVKNPEDSSCTSEI | 28 |
| CD38 Homo sapiens extracellular domain (ECD) | VPRWRQQWSGPGTTKRFPETVLARCVKYTEIHPEMRH VDCQSVWDAFKGAFISKHPCNITEEDYQPLMKLGTQT VPCNKILLWSRIKDLAHQFTQVQRDMFTLEDTLLGYL ADDLTWCGEFNTSKINYQSCPDWRKDCSNNPVSVFW KTVSRRFAEAACDVVHVMLNGSRSKIFDKNSTFGSVE VHNLQPEKVQTLEAWVIHGGREDSRDLCQDPTIKELES IISKRNIQFSCKNIYRPDKFLQCVKNPEDSSCTSEI | 29 |
| CD38 Macaca fascicularis | MANCEFSPVSGDKPCCRLSRRAQVCLGVCLLVLLILVV VVAVVLPRWRQQWSGSGTTSRFPETVLARCVKYTEV HPEMRHVDCQSVWDAFKGAFISKYPCNITEEDYQPLV KLGTQTVPCNKTLLWSRIKDLAHQFTQVQRDMFTLED MLLGYLADDLTWCGEFNTFEINYQSCPDWRKDCSNNP VSVFWKTVSRRFAETACGVVHVMLNGSRSKIFDKNST FGSVEVHNLQPEKVQALEAWVIHGGREDSRDLCQDPT IKELESIISKRNIRFFCKNIYRPDKFLQCVKNPEDSSCLS GI | 30 |
| CD38 Macaca fascicularis extracellular domain (ECD) | LPRWRQQWSGSGTTSRFPETVLARCVKYTEVHPEMRH VDCQSVWDAFKGAFISKYPCNITEEDYQPLVKLGTQT VPCNKTLLWSRIKDLAHQFTQVQRDMFTLEDMLLGYL ADDLTWCGEFNTFEINYQSCPDWRKDCSNNPVSVFWK TVSRRFAETACGVVHVMLNGSRSKIFDKNSTFGSVEV HNLQPEKVQALEAWVIHGGREDSRDLCQDPTIKELESII SKRNIRFFCKNIYRPDKFLQCVKNPEDSSCLSGI | 31 |

FIG. 8

| Linker sequence | SEQ ID NO: |
|---|---|
| (GGGGS)3 | 32 |
| GGS | 33 |
| GGGS | 34 |
| GGGGS | 35 |
| GGGGSGGG | 36 |
| GGSGGGG | 37 |
| GSTSGGGSGGGSGGGGSS | 38 |

FIG. 9A

| CD38 targeting moiety-SLTA | Sequence | SEQ ID NO: |
|---|---|---|
| CD38TM1-SLTA | MKEFTLDFSTAKTYVDSLNVIRSAIGTPLQTISSGGTSLL MIDSGIGDNLFAVDILGFDFTLGRFNNLRLIVERNNLYVT GFVNRTNNVFYRFADFSHVTFPGTTAVTLSADSSYTTLQ RVAGISRTGMQINRHSLTTSYLDLMSHSGTSLTQSVARA MLRFVTVTAEALRFRQIQRGFRTTLDDLSGASYVMTAE DVDLTLNWGRLSSVLPDYHGQDSVRVGRISFGSINAILG SVALILNSHHASAVAAEFPKPSTPPGSSGGAPQSVLTQP PSASGTPGQRVTISCSGSSSNIGSNYVYWYQQLPGTAPKL LIYGNSNRPSGVPDRFSGSKSGTSASLAISGLRSEDEADY YCQSYDSSLSGSGVFGGGTKLTVLGGGGSGGGGSGGG GSGGGGSGGGGSSEVQLLESGGGLVQPGGSLRLSCAAS GFTFSDYYMSWVRQAPGKGLEWVSAISGSGGSTYYADS VKGRFTISRDNSKNTLYLQMNSLRAEDTAVYYCAREHS NYFYGMDVWGQGTLVTVSS | 40 |
| CD38TM2-SLTA | MKEFTLDFSTAKTYVDSLNVIRSAIGTPLQTISSGGTSLL MIDSGIGDNLFAVDILGFDFTLGRFNNLRLIVERNNLYVT GFVNRTNNVFYRFADFSHVTFPGTTAVTLSADSSYTTLQ RVAGISRTGMQINRHSLTTSYLDLMSHSGTSLTQSVARA MLRFVTVTAEALRFRQIQRGFRTTLDDLSGASYVMTAE DVDLTLNWGRLSSVLPDYHGQDSVRVGRISFGSINAILG SVALILNSHHASAVAAEFPKPSTPPGSSGGAPQSVLTQP PSASGTPGQRVTISCSGSSSNIGGNYVYWYQQLPGTAPK LLIYRNNQRPSGVPDRFSGSKSGTSASLAISGLRSEDEAD YYCQSYDSSLSVSVFGGGTKLTVLGGGGGSEVQLLESG GGLVQPGGSLRLSCAASGFTFSSYWMHWVRQAPGKGL EWVSAISGSGGGTFYADSVKGRFTISRDNSKNTLYLQMN SLRAEDTAVYYCAREGETSFGLDVWGQGTLVTVSS | 41 |
| CD38TM3-SLTA | MKEFTLDFSTAKTYVDSLNVIRSAIGTPLQTISSGGTSLL MIDSGIGDNLFAVDILGFDFTLGRFNNLRLIVERNNLYVT GFVNRTNNVFYRFADFSHVTFPGTTAVTLSADSSYTTLQ RVAGISRTGMQINRHSLTTSYLDLMSHSGTSLTQSVARA MLRFVTVTAEALRFRQIQRGFRTTLDDLSGASYVMTAE DVDLTLNWGRLSSVLPDYHGQDSVRVGRISFGSINAILG SVALILNSHHASAVAAEFPKPSTPPGSSGGAPQVQLVQ SGAEVKKPGESLKISCKGSGYSFTSYWIGWVRQMPGKG | 42 |

FIG. 9B

| | | |
|---|---|---|
| | LEWMGIIYPGDSDTRYSPSFQGQVTISADKSISTAYLQWS SLKASDTAMYYCARGPSTGFWSGNYFDYWGQGTLVTV SSGGGGSQTVVTQEPSLTVSPGETVTLTCASSTGAVTSGF YPNWFQQKPGQAPRALIYATNNKYSWTPARFSGSLLGD KAALTLSRVQPEDEADYYCLVYYDGAWVFGGGTKLTV LG | |
| CD38TM4-SLTA | MKEFTLDFSTAKTYVDSLNVIRSAIGTPLQTISSGGTSLL MIDSGIGDNLFAVDILGFDFTLGRFNNLRLIVERNNLYVT GFVNRTNNVFYRFADFSHVTFPGTTAVTLSADSSYTTLQ RVAGISRTGMQINRHSLTTSYLDLMSHSGTSLTQSVARA MLRFVTVTAEALRFRQIQRGFRTTLDDLSGASYVMTAE DVDLTLNWGRLSSVLPDYHGQDSVRVGRISFGSINAILG SVALILNSHHHASAVAAEFPKPSTPPGSSGGAPQVQLVQ SGAEVKKPGESLKISCKGSGYSFTSYWIGWVRQMPGKG LEWMGIIYPGDSDTRYSPSFQGQVTISADKSISTAYLQWS SLKASDTAMYYCARGPSTGFWSGNYFDYWGQGTLVTV SSGGGGSDIQMTQSPSSLSASVGDRVTITCASSTGAVTSG FYPNWFQQKPGQAPRALIYATNNKYSWTPARFSGSLLG DKAALTLSRVQPEDEADYYCLVYYDGAWVFGGGTKLT VLG | 43 |
| CD38TR1-SLTA | MKEFTLDFSTAKTYVDSLNVIRSAIGTPLQTISSGGTSLL MIDSGSGDNLFAVDVRGIDPEEGRFNNLRLIVERNNLYV TGFVNRTNNVFYRFADFSHVTFPGTTAVTLSGDSSYTTL QRVAGISRTGMQINRHSLTTSYLDLMSHSGTSLTQSVAR AMLRFVTVTAEALRFRQIQRGFRTTLDDLSGRSYVMTAE DVDLTLNWGRLSSVLPDYHGQDSVRVGRISFGSINAILG SVALILNCHHHASAVAAEFPKPSTPPGSSGGAPDIQMTQS PSSLSASVGDRVTITCKASEDIYNRLTWYQQKPGKAPKL LISGATSLETGVPSRFSGSGSGTDFTFTISSLQPEDIATYYC QQYWSNPYTFGQGTKVEIKGGGGSQVQLQESGPGLVRP SQTLSLTCTVSGFSLTSYGVHWVRQPPGRGLEWIGVMW RGGSTDYNAAFMSRLNITKDNSKNQVSLRLSSVTAADT AVYYCAKSMITTGFVMDSWGQGSLVTVSS | 44 |

FIG. 10A

Human IgG1 constant region
ASTKGPSVFPLAPSSKSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMHEALHNHYTQKSLSLSP
GK (SEQ ID NO:39)

Human IgG1 D265A constant region
ASTKGPSVFPLAPSSKSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVV[A]VSHEDPEVKFNWYVDGVE
VHNAKTKPREEQYNSTYRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMHEALHNHYTQKSLSLSP
GK (SEQ ID NO:45)

Human IgG1 N297A constant region
ASTKGPSVFPLAPSSKSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSHEDPEVKFNWYVDGVE
VHNAKTKPREEQY[A]STYRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMHEALHNHYTQKSLSLSP
GK (SEQ ID NO:46)

Human IgG2 constant region
ASTKGPSVFPLAPCSRSTSESTAALGCLVKDYFPEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMISRTPEVTCVVVDVSHEDPEVQFNWYVDGVEVH
NAKTKPREEQFNSTFRVVSVLTVVHQDWLNGKEYKCKVSNKGLPAPIEKTISKTKGQPREPQVYTLPPSREEMTKNQVSLTC
LVKGFYPSDIAVEWESNGQPENNYKTTPPMLDSDGSFFLYSKLTVDKSRWQQGNVFSCSVMHEALHNHYTQKSLSLSPGK
(SEQ ID NO:47)

FIG. 10B

Human IgG3 constant region
ASTKGPSVFPLAPCSRSTSGGTAALGCLVKDYFPEPVTVSWNSGALTSGVHTFPAVLQSSGLYSLSSVVTVPSSSLGTQTYTC
NVNHKPSNTKVDKRVELKTPLGDTTHTCPRCPEPKSCDTPPPCPRCPEPKSCDTPPPCPRCPEPKSCDTPPPCPRCPAPELLGGP
SVFLFPPKPKDTLMISRTPEVTCVVVDVSHEDPEVQFKWYVDGVEVHNAKTKPREEQYNSTFRVVSVLTVLHQDWLNGKE
YKCKVSNKALPAPIEKTISKTKGQPREPQVYTLPPSREEMTKNQVSLTCLVKGFYPSDIAVEWESSGQPENNYNTTPPMLDSD
GSFFLYSKLTVDKSRWQQGNIFSCSVMHEALHNRFTQKSLSLSPGK (SEQ ID NO:48)

Human IgG4 constant region (Wild Type)
ASTKGPSVFPLAPCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCPSCPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQEGNVFSCSVMHEALHNHYTQKSLSLSPGK
(SEQ ID NO:49)

Human IgG4 constant region (S241P hinge mutant)
ASTKGPSVFPLAPCSRSTSESTAALGCLVKDYFPEPVTVSWNSGALTSGVHTFPAVLQSSGLYSLSSVVTVPSSSLGTKTYTCN
VDHKPSNTKVDKRVESKYGPPCP[P]CPAPEFLGGPSVFLFPPKPKDTLMISRTPEVTCVVVDVSQEDPEVQFNWYVDGVEVHN
AKTKPREEQFNSTYRVVSVLTVLHQDWLNGKEYKCKVSNKGLPSSIEKTISKAKGQPREPQVYTLPPSQEEMTKNQVSLTCL
VKGFYPSDIAVEWESNGQPENNYKTTPPVLDSDGSFFLYSRLTVDKSRWQEGNVFSCSVMHEALHNHYTQKSLSLSPGK
(SEQ ID NO:50)

Human kappa light chain
RTVAAPSVFIFPPSDEQLKSGTASVVCLLNNFYPREAKVQWKVDNALQSGNSQESVTEQDSKDSTYSLSSTLTLSKADYEKH
KVYACEVTHQGLSSPVTKSFNRGEC (SEQ ID NO:51)

Human lambda light chain
GQPKAAPSVTLFPPSSEELQANKATLVCLISDFYPGAVTVAWKADSSPVKAGVETTTPSKQSNNKYAASSYLSLTPEQWKSH
RSYSCQVTHEGSTVEKTVAPTECS (SEQ ID NO:52)

FIG. 11C

CD38TM3 VL
QTVVTQEPSLTVSPGETVTLTCASSTGAVTSGFYPNWFQQKPGQAPRALIYATNNKYSWTPARFSGSLLGDKAALTLSRVQP
EDEADYYCLVYDGAWVFGGGTKLTVLG (SEQ ID NO:5)

CD38TR1 VL
DIQMTQSPSSLSASVGDRVTITCKASEDIYNRLTWYQQKPGKAPKLLISGATSLETGVPSRFSGSGSGTDFTFTISSLQPEDIAT
YYCQQYWSNPYTFGQGTKVEIK (SEQ ID NO:27)

CD38TM4 VL
DIQMTQSPSSLSASVGDRVTITCASSTGAVTSGFYPNWFQQKPGQAPRALIYATNNKYSWTPARFSGSLLGDKAALTLSRVQ
PEDEADYYCLVYDGAWVFGGGTKLTVLG (SEQ ID NO:25)

ANTI-CD38 BINDING DOMAINS

I. CROSS REFERENCE TO RELATED APPLICATIONS

This application is a Continuation of U.S. application Ser. No. 16/751,107, filed Jan. 23, 2020, entitled "ANTI-CD38 BINDING DOMAINS", which claims priority under 35 U.S.C. § 119 to U.S. Provisional Application No. 62/795,855, filed Jan. 23, 2019. The entire contents of these applications are incorporated herein by reference in their entirety.

II. REFERENCE TO AN ELECTRONIC SEQUENCE LISTING

The contents of the electronic sequence listing (T083370003US03-SEQ-ZJG.xml; Size: 87,072 bytes; and Date of Creation: Jul. 1, 2022) is herein incorporated by reference in its entirety.

III. BACKGROUND OF THE INVENTION

CD38, also known as cyclic ADP ribose hydrolase, is a type II transmembrane glycoprotein with a long C-terminal extracellular domain and a short N-terminal cytoplasmic domain. CD38 is a member of a group of related membrane bound or soluble enzymes, comprising CD157 and Aplysia ADPR cyclase. This family of enzymes has the unique capacity to convert NAD to cyclic ADP ribose or nicotinic acid-adenine dinucleotide phosphate.

In addition, CD38 has been reported to be involved in $Ca^{2+}$ mobilization and in the signal transduction through tyrosine phosphorylation of numerous signaling molecules, including phospholipase Cγ, ZAP-70, syk, and c-cbl. Based on these observations, CD38 was proposed to be an important signaling molecule in the maturation and activation of lymphoid cells during their normal development.

CD38 is found to be expressed on the surface of many immune cells, including B cells, plasma cells, CD4+ T cells, CD8+ T cells, NK cells, NKT cells, mature dendritic cells (DCs) and activated monocytes. Among hematopoietic cells, CD38 has been found to be involved in functional effects such as lymphocyte proliferation, cytokine release, regulation of B and myeloid cell development and survival, and induction of dendritic cell maturation (FIG. 1).

The presumed natural ligand of CD38 is CD31 (PECAM-1; Platelet Endothelial Cell Adhesion Molecule-1), which is a 130 kD member of the immunoglobulin superfamily which is expressed on the surface of circulating platelets, neutrophils, monocytes, and naïve B-lymphocytes. Functionally, CD31 is thought to act as an adhesion molecule, and the interaction of CD38 with CD31 may act in promoting survival of leukemia cells.

CD38 is upregulated in many hematopoeitic malignancies and in cell lines derived from various hematopoietic malignancies including non-Hodgkin's lymphoma (NHL), Burkitt's lymphoma (BL), multiple myeloma (MM), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML). CD38 has been hence used as a prognostic marker in leukemia.

In spite of the recent progress in the discovery and development of anti-cancer agents, many forms of cancer involving CD38-expressing tumors still have a poor prognosis. Thus, there is a need for improved methods for treating such forms of cancer, and a need to develop anti-CD38 antibodies with improved characteristics despite existing antibodies on the market.

IV. BRIEF SUMMARY OF THE INVENTION

This invention relates to a composition that includes a novel anti-CD38 antigen binding domain.

In one aspect, the composition includes an anti-CD38 antigen binding domain which contains a variable heavy domain (VH) comprising a vhCDR1 with an amino acid sequence of SEQ ID NO:2, a vhCDR2 with an amino acid sequence of SEQ ID NO:3 and a vhCDR3 with an amino acid sequence of SEQ ID NO:4; and a variable light domain (VL) comprising a vlCDR1 with an amino acid sequence of SEQ ID NO:6, a vlCDR2 with an amino acid sequence of SEQ ID NO:7 and a vlCDR3 with an amino acid sequence of SEQ ID NO:8.

In some embodiments, said composition includes an anti-CD38 antigen binding domain that contains a variable heavy domain with an amino acid sequence identical to SEQ ID NO:1, and a variable light domain with an amino acid sequence identical to SEQ ID NO:5. In some embodiments, said composition includes an anti-CD38 antigen binding domain that contains a variable heavy domain with an amino acid sequence identical to SEQ ID NO:1, and a variable light domain with an amino acid sequence identical to SEQ ID NO:25.

In another aspect, the composition includes an anti-CD38 antigen binding domain which contains a variable heavy domain (VH) comprising a vhCDR1 with an amino acid sequence of SEQ ID NO:10, a vhCDR2 with an amino acid sequence of SEQ ID NO:11 and a vhCDR3 with an amino acid sequence of SEQ ID NO:12; and a variable light domain (VL) comprising a vlCDR1 with an amino acid sequence of SEQ ID NO:14, a vlCDR2 with an amino acid sequence of SEQ ID NO:15 and a vlCDR3 with an amino acid sequence of SEQ ID NO:16.

In some embodiments, said composition includes an anti-CD38 antigen binding domain that contains a variable heavy domain with an amino acid sequence identical to SEQ ID NO:9, and a variable light domain with an amino acid sequence identical to SEQ ID NO:13.

In another aspect, the composition includes an anti-CD38 antigen binding domain which contains a variable heavy domain (VH) comprising a vhCDR1 with an amino acid sequence of SEQ ID NO:18, a vhCDR2 with an amino acid sequence of SEQ ID NO:19 and a vhCDR3 with an amino acid sequence of SEQ ID NO:20; and a variable light domain (VL) comprising a vlCDR1 with an amino acid sequence of SEQ ID NO:22, a vlCDR2 with an amino acid sequence of SEQ ID NO:23 and a vlCDR3 with an amino acid sequence of SEQ ID NO:24.

In some embodiments, said composition includes an anti-CD38 antigen binding domain that contains a variable heavy domain with an amino acid sequence identical to SEQ ID NO:17, and a variable light domain with an amino acid sequence identical to SEQ ID NO:21.

In another aspect, the composition includes an anti-CD38 antigen binding domain which contains a variable heavy domain (VH) comprising a vhCDR1 with an amino acid sequence of SEQ ID NO:54, a vhCDR2 with an amino acid sequence of SEQ ID NO:55 and a vhCDR3 with an amino acid sequence of SEQ ID NO:56; and a variable light domain (VL) comprising a vlCDR1 with an amino acid sequence of SEQ ID NO:58, a vlCDR2 with an amino acid sequence of SEQ ID NO:59 and a vlCDR3 with an amino acid sequence of SEQ ID NO:60.

In some embodiments, said composition includes an anti-CD38 antigen binding domain that contains a variable heavy domain with an amino acid sequence identical to SEQ ID NO:53, and a variable light domain with an amino acid sequence identical to SEQ ID NO:57.

In some embodiments, said composition that includes an anti-CD38 antigen binding domain as described herein comprises a variable heavy domain and a variable light domain on a single polypeptide. In some embodiments, the single polypeptide includes a scFv linker, a variable heavy domain and a variable light domain in the orientation from N- to C-terminus of VH-scFv linker-VL or VL-scFv linker-VH.

In some embodiments, said composition that includes an anti-CD38 antigen binding domain as described herein comprises a first polypeptide which includes a variable heavy domain and a second polypeptide which includes a variable light domain.

In some embodiments, said composition that includes an anti-CD38 antigen binding domain as described herein is antibody that contains a heavy chain which includes a variable heavy domain, and a light chain which includes a variable light domain. In some embodiments, said antibody contains a heavy chain which includes a variable heavy domain and a heavy constant domain selected from the heavy constant domains of human IgG1, IgG2 and IgG4, and the variants thereof. In some embodiments, said antibody contains a heavy chain which includes a variable heavy domain and a heavy constant domain of human IgG1 or the variants thereof. In some embodiments, said antibody contains a heavy chain which includes a variable heavy domain and a heavy constant domain selected from the heavy constant domains of human IgG1 variant with ablated FcγR binding. In some embodiments, said antibody contains a heavy chain which includes a variable heavy domain and a heavy constant domain selected from the heavy constant domains of human IgG4 variant with an S228P amino acid substitution.

This invention also relates to a nucleic acid composition encoding a variable heavy domain and a variable light domain. In some embodiments, said nucleic acid composition contains a first nucleic acid encoding a variable heavy domain and a second nucleic acid encoding a variable heavy domain. In some embodiments, said nucleic acid composition contains a single nucleic acid encoding a variable heavy domain and a variable light domain.

Another aspect of the invention relates to an expression vector composition containing any one of the nucleic acid compositions described herein; and a host cell containing any one of said expression vector compositions described herein. In some embodiments, said expression vector composition includes a first expression vector that contains said first nucleic acid, and a second expression vector that contains said second nucleic acid described herein. In some embodiments, said expression vector composition includes said nucleic acid composition that contains a single nucleic acid encoding a variable heavy domain and a variable light domain.

This invention further relates to a method of making any of said compositions containing an anti-CD38 antigen binding domain described herein. The method includes culturing said host cell under conditions wherein the anti-CD38 antigen binding domain is expressed, and recovering said composition.

Also included in this invention is a method of treating multiple myeloma using an effective amount of any of said compositions containing an anti-CD38 antigen binding domain described herein.

FIG. 4 shows critical contact residues on CD38 extracellular domain for anti-CD38 binding clone CD38TM4 (F216, L262, C119, L124, C201, L230, C254, C275) and anti-CD38 monoclonal antibody daratumumab (S274).

FIGS. 5A-5B show binding of anti-CD38 binding clones (in an scFv-SLTA fusion format) to CD38-expressing MOLP-8 cells in the presence of anti-CD38 antibodies daratumumab (Dara), HB-7, AT13-5 and OKT-10 and several fusion proteins. CD38 Targeting reference molecule #1 (CD38TR1) is also in the format of scFv-SLTA fusion protein. FIG. 5C shows competitive binding of anti-CD38 binding clones including CD38 Targeting reference molecule #1 (CD38TR1) in an scFv-SLTA fusion format to CD38-expressing MOLP-8 cells. All signals were detected by flow cytometry. FIG. 5D is a table summarizing the binding of anti-CD38 binding clones in an scFv-SLTA fusion protein format (top row) in the presence of anti-CD38 binding clones (in scFv alone format) (first left column).

FIGS. 6A-6G depict the sequences of the variable heavy and variable light domains of CD38TM1, CD38TM2, CD38TM3, CD38TM4, CD38TM5, CD38TM6 and CD38TR1 as well as the CDRs (underlined in the full domains).

FIG. 7 shows the sequences of the CD38 target antigens of the invention.

FIG. 8 depicts some linker sequences.

FIGS. 9A-9B depict the sequences of some Shiga toxin proteins fused to anti-CD38 binding domains as used in the examples.

FIGS. 10A-10B depict a number of IgG heavy constant domain "backbones", based on human IgG1, IgG2 and IgG4, including some standard variants, as well as the sequences for the constant light kappa and constant light lambda sequences. As will be appreciated by those in the art, and as described below, any of these backbones can be combined with the variable heavy and variable light domains of CD38TM1, CD38TM2, CD38TM3, CD38TM4, CD38TM5, CD38TM6 and CD38TR1.

FIGS. 11A-11B show purification of CD38TM3-SLTA and CD38TM4-SLTA by IMAC column and protein L (Pro-L) column respectively. MW marker indicates where molecular weight markers are located. FIG. 11C shows the first 21 amino acids of CD38TM3 (underlined) is replaced with first 22 amino acids of CD38TR1 (underlined) to derive CD38TM4.

Figure 12:
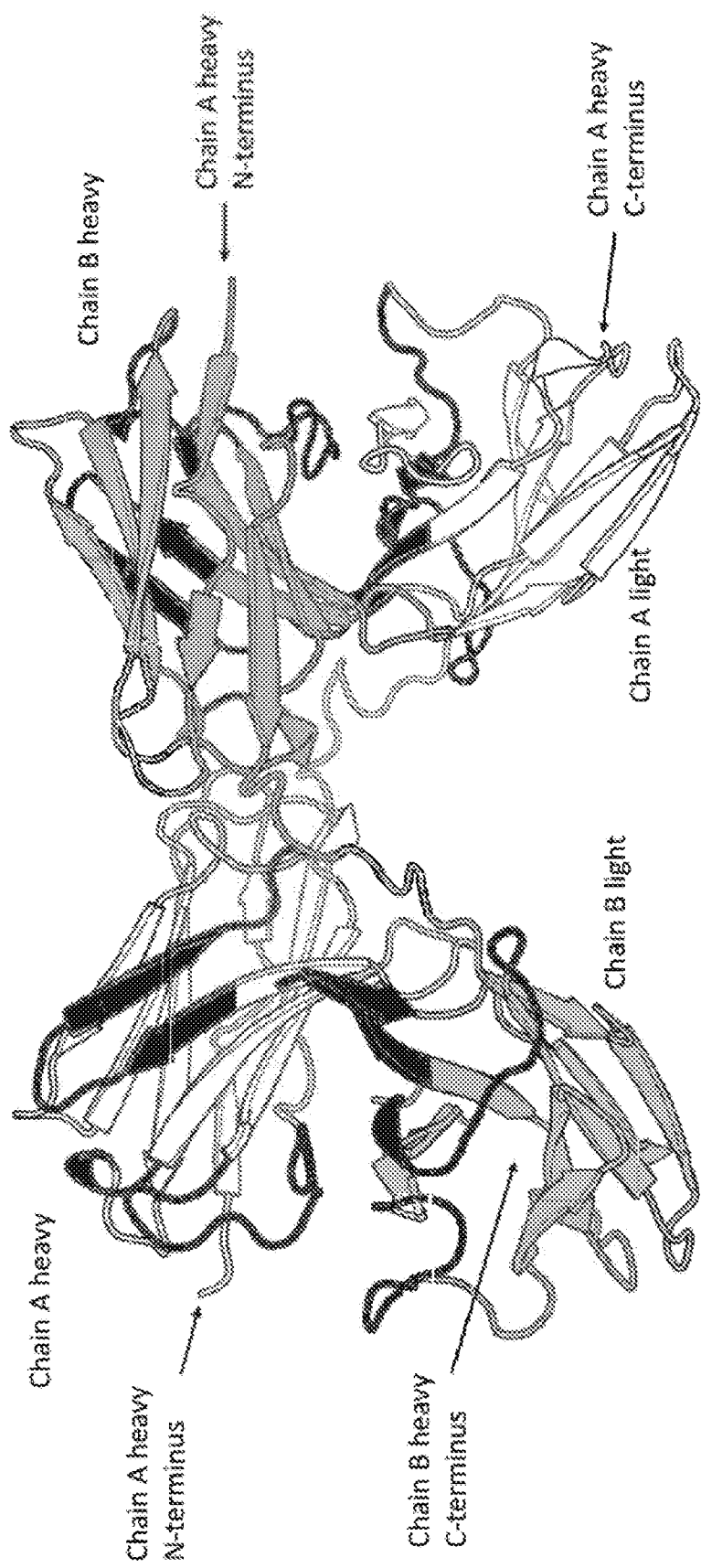

FIG. 12 shows illustration of the X-ray structure of a diabody formed by two identical scFvs, each containing VH-GGGGS-VL from N- to C-terminus, wherein the VH and VL are from CD38TM4. The VH of one scFv chain (chain A) complexes with the VL of the other scFV chain (chain B) to form a CD38 binding domain.

V. DETAILED DESCRIPTION OF THE INVENTION

A. Overview

Increased expression of CD38 has been associated with a variety of diseases of hematopoietic origin. Such diseases include but are not restricted to, multiple myeloma, chronic lymphoblastic leukemia, B-cell chronic lymphocytic leukemia, acute lymphoblastic leukemia, including B-cell acute lymphocytic leukemia, Waldenstrom macroglobulinemia, primary systemic amyloidosis, mantle-cell lymphoma, prolymphocytic/myelocytic leukemia, acute myeloid leukemia, chronic myeloid leukemia, follicular lymphoma, NK-cell leukemia and plasma-cell leukemia. As such, CD38 provides a useful target in the treatment of diseases of the hematopoietic system. Several anti-CD38 antibodies are in clinical trials for the treatment of CD38-associated cancers. Accordingly, antibodies to CD38 are useful to treat and diagnose cancer.

The present invention provides anti-CD38 binding domains that are able to bind human and cynomolgus CD38 with high affinity. Furthermore, the anti-CD38 binding domains disclosed here are capable of binding to CD38 in the presence of daratumumab, and hence provide an advantage in clinical applications not seen in some of the existing anti-CD38 antibodies in clinical testing.

B. Definitions

In order that the application may be more completely understood, several definitions are set forth below. Such definitions are meant to encompass grammatical equivalents.

By "ablation" herein is meant a decrease or removal of activity. In some embodiments, it is useful to remove activity from the constant domains of the antibodies. Thus, for example, "ablating FcγR binding" means the Fc region amino acid variant has less than 50% starting binding to an FcγR as compared to an Fc region not containing the specific variant, with less than 70-80-90-95-98% loss of activity being preferred, and in general, with the activity being below the level of detectable binding in a Biacore assay. For example, one ablation variant in the IgG1 constant region is the N297A variant, which removes the native glycosylation site and significantly reduces the FcγRIIIa binding and thus reduces the antibody dependent cell-mediated cytotoxicity (ADCC).

By "ADCC" or "antibody dependent cell-mediated cytotoxicity" as used herein is meant the cell-mediated reaction wherein nonspecific cytotoxic cells that express FcγRs recognize bound antibody on a target cell and subsequently cause lysis of the target cell. ADCC is correlated with binding to FcγRIIIa; increased binding to FcγRIIIa leads to an increase in ADCC activity.

By "antigen binding domain" or "ABD" herein is meant a set of six Complementary Determining Regions (CDRs) that, when present as part of a polypeptide sequence, specifically binds a target antigen as discussed herein. Thus, an "anti-CD38 antigen binding domain" binds CD38 antigen as outlined herein. As is known in the art, these CDRs are generally present as a first set of variable heavy CDRs (vhCDRs or VHCDRs) and a second set of variable light CDRs (vlCDRs or VLCDRs), each comprising three CDRs: vhCDR1, vhCDR2, vhCDR3 for the heavy chain and vlCDR1, vlCDR2 and vlCDR3 for the light chain. As is understood in the art, the CDRs are separated by framework regions in each of the heavy variable and light variable regions: for the light variable region, these are (VL)FR1-vlCDR1-(VL)FR2-vlCDR2-(VL)FR3-vlCDR3-(VL)FR4, and for the heavy variable region, these are (VH)FR1-vhCDR1-(VH)FR2-vhCDR2-(VH)FR3-vhCDR3-(VH) FR4. Antigen binding domains of the invention can be embodied in multiple formats, for example, in Fab, Fv and scFv. In an "Fab" format, the set of 6 CDRs are contributed by two different polypeptide sequences, the heavy variable region (vh or VH; containing the vhCDR1, vhCDR2 and vhCDR3) and the light variable region (vl or VL; containing the vlCDR1, vlCDR2 and vlCDR3), with the C-terminus of the VH being attached to the N-terminus of the CH1 domain of the heavy chain and the C-terminus of the VL being attached to the N-terminus of the constant light domain (and thus forming the light chain). Heavy variable regions and light variable regions together form Fvs, which can be either scFvs or Fabs, as outlined herein. Thus, in some cases, the six CDRs of the antigen binding domain are contributed by a VH and VL. In an scFv format, the VH and VL are covalently attached, generally through the use of a linker as outlined herein, into a single polypeptide sequence, which can be either (starting from the N-terminus) VH-linker-VL or VL-linker-VH.

By "linker" herein is meant a domain linker that joins two protein domains together, such as are used in scFv and/or other protein and protein fusion structures. Generally, there are a number of suitable linkers that can be used, including traditional peptide bonds, generated by recombinant techniques that allows for recombinant attachment of the two domains with sufficient length and flexibility to allow each domain to retain its biological function. The linker peptide may predominantly include the following amino acid residues: Gly, Ser, Ala, or Thr. The linker peptide should have a length that is adequate to link two molecules in such a way that they assume the correct conformation relative to one another so that they retain the desired activity. In one embodiment, the linker is from about 1 to 50 amino acids in length, preferably about 1 to 30 amino acids in length. In one embodiment, linkers of 1 to 20 amino acids in length may be used, with from about 5 to about 10 amino acids finding use in some embodiments. Useful linkers include glycine-serine polymers, including for example (GS)n, (GSGGS)n, (GGGGS)n, and (GGGS)n, where n is an integer of at least one (and generally from 3 to 4), glycine-alanine polymers, alanine-serine polymers, and other flexible linkers. Alternatively, a variety of non-proteinaceous polymers, including but not limited to polyethylene glycol (PEG), polypropylene glycol, polyoxyalkylenes, or copolymers of polyethylene glycol and polypropylene glycol, may find use as linkers. Other linker sequences may include any sequence of any length of CL/CH1 domain but not all residues of CL/CH1 domain; for example, the first 5-12 amino acid residues of the CL/CH1 domains. Linkers can also be derived from immunoglobulin light chain, for example Cκ or Cλ. Linkers can be derived from immunoglobulin heavy chains of any isotype, including for example Cγ1, Cγ2, Cγ3, Cγ4, Cα1, Cα2, Cδ, Cε, and Cμ. Linker sequences may also be derived from other proteins such as Ig-like proteins (e.g., TCR, FcR, KIR), hinge region-derived sequences, and other natural sequences from other proteins. While any suitable linker can be used, many embodiments utilize a glycine-serine polymer, including for example (GS)n, (GSGGS)n, (GGGGS)n, and (GGGS)n, where n is an integer of at least one (and generally from 2 to 3 to 4 to 5). "scFv linkers" generally include these glycine-serine polymers, such as those shown in FIG. 8. In general, scFv linkers are long enough to allow the VL and VH domains to properly associate to form an antigen binding domain (ABD) on a single polypeptide.

The term "antibody" is used in the broadest sense and includes, for example, an intact immunoglobulin or an antigen binding portion. Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). Human light chains are classified as kappa and lambda light chains. The present invention is directed to antibodies or antibody fragments (antibody monomers) that generally are based on the IgG class, which has several subclasses, including, but not limited to IgG1, IgG2, IgG3, and IgG4. In general, IgG1, IgG2 and IgG4 are used more frequently than IgG3. It should be noted that IgG1 has different allotypes with polymorphisms at 356 (D or E) and 358 (L or M). The sequences depicted herein use the 356D/358M allotype, however the other allotype is included herein. That is, any sequence inclusive of an IgG1 Fc domain included herein can have 356E/358L replacing the 356D/358M allotype.

Thus, "isotype" as used herein is meant any of the subclasses of immunoglobulins defined by the chemical and antigenic characteristics of their constant regions.

The amino-terminal portion of each chain includes a variable region of about 100 to 110 or more amino acids primarily responsible for antigen recognition, generally referred to in the art and herein as the "Fv domain" or "Fv region". In the variable region, three loops are gathered for each of the V domains of the heavy chain and light chain to form an antigen-binding site. Each of the loops is referred to as a complementarity-determining region (hereinafter referred to as a "CDR"), in which the variation in the amino acid sequence is most significant. "Variable" refers to the fact that certain segments of the variable region differ extensively in sequence among antibodies. Variability within the variable region is not evenly distributed. Instead, the V regions consist of relatively invariant stretches called framework regions (FRs) of 15-30 amino acids separated by shorter regions of extreme variability called "hypervariable regions" that are each 9-15 amino acids long or longer.

Each VH and VL is composed of three hypervariable regions ("complementary determining regions," "CDRs") and four FRs, arranged from amino-terminus to carboxy-terminus in the following order: FR1-CDR1-FR2-CDR2-FR3-CDR3-FR4.

The hypervariable region generally encompasses amino acid residues from about amino acid residues 24-34 (LCDR1; "L" denotes light chain), 50-56 (LCDR2) and 89-97 (LCDR3) in the light chain variable region and around about 31-35B (HCDR1; "H" denotes heavy chain), 50-65 (HCDR2), and 95-102 (HCDR3) in the heavy chain variable region; Kabat et al., SEQUENCES OF PROTEINS OF IMMUNOLOGICAL INTEREST, 5th Ed. Public Health Service, National Institutes of Health, Bethesda, Md. (1991) and/or those residues forming a hypervariable loop (e.g. residues 26-32 (LCDR1), 50-52 (LCDR2) and 91-96 (LCDR3) in the light chain variable region and 26-32 (HCDR1), 53-55 (HCDR2) and 96-101 (HCDR3) in the heavy chain variable region; Chothia and Lesk (1987). J. Mol. Biol. 196:901-917. Specific CDRs of the invention are described below.

As will be appreciated by those in the art, the exact numbering and placement of the CDRs can be different among different numbering systems. However, it should be understood that the disclosure of a variable heavy and/or variable light sequence includes the disclosure of the associated (inherent) CDRs. Accordingly, the disclosure of each variable heavy region is a disclosure of the vhCDRs (e.g. vhCDR1, vhCDR2 and vhCDR3) and the disclosure of each variable light region is a disclosure of the vlCDRs (e.g. vlCDR1, vlCDR2 and vlCDR3).

A useful comparison of CDR numbering is as below, see Lafranc et al., Dev. Comp. Immunol. 27(1):55-77 (2003):

TABLE 1

|  | Kabat + Chothia | IMGT | Kabat | AbM | Chothia | Contact |
| --- | --- | --- | --- | --- | --- | --- |
| vhCDR1 | 26-35 | 27-38 | 31-35 | 26-35 | 26-32 | 30-35 |
| vhCDR2 | 50-65 | 56-65 | 50-65 | 50-58 | 52-56 | 47-58 |
| vhCDR3 | 95-102 | 105-117 | 95-102 | 95-102 | 95-102 | 93-101 |
| vlCDR1 | 24-34 | 27-38 | 24-34 | 24-34 | 24-34 | 30-36 |
| vlCDR2 | 50-56 | 56-65 | 50-56 | 50-56 | 50-56 | 46-55 |
| vlCDR3 | 89-97 | 105-117 | 89-97 | 89-97 | 89-97 | 89-96 |

Throughout the present specification, the Kabat numbering system is generally used when referring to a residue in the variable domain (approximately, residues 1-107 of the light chain variable region and residues 1-113 of the heavy chain variable region) and the EU numbering system for Fc regions (e.g, Kabat et al., supra (1991)).

The present invention provides a large number of different CDR sets. In this case, a "full CDR set" comprises the three variable light and three variable heavy CDRs, e.g. a vlCDR1, vlCDR2, vlCDR3, vhCDR1, vhCDR2 and vhCDR3. These can be part of a larger variable light or variable heavy domain, respectfully. In addition, as more fully outlined herein, the variable heavy and variable light domains can be on separate polypeptide chains, when a heavy and light chain is used (for example when Fabs are used), or on a single polypeptide chain in the case of scFv sequences.

The CDRs contribute to the formation of the antigen-binding, or more specifically, epitope binding site of antibodies.

"Epitope" refers to a determinant that interacts with a specific antigen binding site in the variable region of an antibody molecule known as a paratope. Epitopes are groupings of molecules such as amino acids or sugar side chains and usually have specific structural characteristics, as well as specific charge characteristics. A single antigen may have more than one epitope. The epitope may comprise amino acid residues directly involved in the binding (also called immunodominant component of the epitope) and other amino acid residues, which are not directly involved in the binding, such as amino acid residues which are effectively blocked by the specifically antigen binding peptide; in other words, the amino acid residue is within the footprint of the specifically antigen binding peptide. Epitopes may be either conformational or linear. A conformational epitope is produced by spatially juxtaposed amino acids from different segments of the linear polypeptide chain. A linear epitope is one produced by adjacent amino acid residues in a polypeptide chain. Conformational and non-conformational epitopes may be distinguished in that the binding to the former but not the latter is lost in the presence of denaturing solvents.

By "modification" herein is meant an amino acid substitution, insertion, and/or deletion in a polypeptide sequence or an alteration to a moiety chemically linked to a protein. For example, a modification may be an altered carbohydrate or PEG structure attached to a protein. By "amino acid modification" herein is meant an amino acid substitution, insertion, and/or deletion in a polypeptide sequence. For clarity, unless otherwise noted, the amino acid modification is always to an amino acid coded for by DNA, e.g. the 20 amino acids that have codons in DNA and RNA.

By "amino acid substitution" or "substitution" herein is meant the replacement of an amino acid at a particular position in a parent polypeptide sequence with a different amino acid. In particular, in some embodiments, the substitution is to an amino acid that is not naturally occurring at the particular position, either not naturally occurring within the organism or in any organism. For example, the substitution N297A refers to a variant polypeptide, in this case an Fc variant, in which the asparagine at position 297 is replaced with alanine. For clarity, a protein which has been engineered to change the nucleic acid coding sequence but not change the starting amino acid (for example exchanging CGG (encoding arginine) to CGA (still encoding arginine) to increase host organism expression levels) is not an "amino acid substitution"; that is, despite the creation of a new gene encoding the same protein, if the protein has the same amino acid at the particular position that it started with, it is not an amino acid substitution.

By "amino acid insertion" or "insertion" as used herein is meant the addition of an amino acid sequence at a particular position in a parent polypeptide sequence. For example, –233E or 233E designates an insertion of glutamic acid after position 233 and before position 234. Additionally, –233ADE or A233ADE designates an insertion of AlaAspGlu after position 233 and before position 234.

By "amino acid deletion" or "deletion" as used herein is meant the removal of an amino acid sequence at a particular position in a parent polypeptide sequence. For example, E233- or E233 #, E233( ) or E233del designates a deletion of glutamic acid at position 233. Additionally, EDA233- or EDA233 #designates a deletion of the sequence GluAspAla that begins at position 233.

By "variant protein" or "protein variant", or "variant" as used herein is meant a protein that differs from that of a parent protein by virtue of at least one amino acid modification. Protein variant may refer to the protein itself, a composition comprising the protein, or the amino sequence that encodes it. Preferably, the protein variant has at least one amino acid modification compared to the parent protein, e.g. from about one to about seventy amino acid modifications, and preferably from about one to about five amino acid modifications compared to the parent. As described below, in some embodiments the parent polypeptide, for example an Fc parent polypeptide, is a human wild type sequence, such as the Fc region from IgG1, IgG2, IgG3 or IgG4, although human sequences with variants can also serve as "parent polypeptides". The protein variant sequence herein will preferably possess at least about 80% identity with a parent protein sequence, and most preferably at least about 90% identity, more preferably at least about 95-98-99% identity. Variant protein can refer to the variant protein itself, compositions comprising the protein variant, or the DNA sequence that encodes it.

Accordingly, by "antibody variant" or "variant antibody" as used herein is meant an antibody that differs from a parent antibody by virtue of at least one amino acid modification, "IgG variant" or "variant IgG" as used herein is meant an antibody that differs from a parent IgG (again, in many cases, from a human IgG sequence) by virtue of at least one amino acid modification. "Immunoglobulin variant" or "variant immunoglobulin" as used herein is meant an immunoglobulin sequence that differs from that of a parent immunoglobulin sequence by virtue of at least one amino acid modification. "Fc variant" or "variant Fc" as used herein is meant a protein comprising an amino acid modification in an Fc domain. The Fc variants of the present invention are defined according to the amino acid modifications that compose them. Thus, for example, S241P or S228P is a hinge variant with the substitution proline at position 228 relative to the parent IgG4 hinge polypeptide, wherein the numbering 5228P is according to the EU index and the S241P is the Kabat numbering. Likewise, M252Y/S254T/T256E defines an Fc variant with the substitutions M252Y, S254T and T256E relative to the parent Fc polypeptide (these mutations increase binding of the Fc domain to the FcRn receptor, thus increasing the half life of the molecule). The identity of the wild type amino acid may be unspecified, in which case the aforementioned variant is referred to as 252Y/254T/256E. It is noted that the order in which substitutions are provided is arbitrary, that is to say that, for example, 252Y/254T/256E is the same Fc variant as 254T/252Y/256E, and so on. For all positions discussed in the present invention that relate to antibodies, unless otherwise noted, amino acid position numbering is according to Kabat for the variable region numbering and is according to the EU index for the constant regions, including the Fc region. The EU index or EU index as in Kabat or EU numbering scheme refers to the numbering of the EU antibody (Edelman et al., 1969, Proc Natl Acad Sci USA 63:78-85, hereby entirely incorporated by reference.) The modification can be an addition, deletion, or substitution. Substitutions can include naturally occurring amino acids and, in some cases, synthetic amino acids. Examples include U.S. Pat. No. 6,586,207; WO 98/48032; WO 03/073238; US2004-0214988A1; WO 05/35727A2; WO 05/74524A2; J. W. Chin et al., (2002), Journal of the American Chemical Society 124:9026-9027; J. W. Chin, & P. G. Schultz, (2002), ChemBioChem 11:1135-1137; J. W. Chin, et al., (2002), PICAS United States of America 99:11020-11024; and, L Wang, & P. G. Schultz, (2002), Chem. 1-10, all entirely incorporated by reference.

As used herein, "protein" herein is meant at least two covalently attached amino acids, which includes proteins, polypeptides, oligopeptides and peptides. The peptidyl group comprises naturally occurring amino acids and peptide bonds, or synthetic peptidomimetic structures, i.e. "analogs", such as peptoids (see Simon et al., PNAS USA 89(20):9367 (1992), entirely incorporated by reference). The amino acids may either be naturally occurring or synthetic (e.g. not an amino acid that is coded for by DNA); as will be appreciated by those in the art. For example, homophenylalanine, citrulline, ornithine and norleucine are considered synthetic amino acids for the purposes of the invention, and both D- and L- (R or S) configured amino acids may be utilized. The variants of the present invention may comprise modifications that include the use of synthetic amino acids incorporated using, for example, the technologies developed by Schultz and colleagues, including but not limited to methods described by Cropp & Shultz, 2004, Trends Genet. 20(12):625-30, Anderson et al., 2004, Proc Natl Acad Sci USA 101 (2):7566-71, Zhang et al., 2003, 303(5656):371-3, and Chin et al., 2003, Science 301(5635): 964-7, all entirely incorporated by reference. In addition, polypeptides may include synthetic derivatization of one or more side chains or termini, glycosylation, PEGylation, circular permutation, cyclization, linkers to other molecules, fusion to proteins or protein domains, and addition of peptide tags or labels.

By "residue" as used herein is meant a position in a protein and its associated amino acid identity. For example, Asparagine 297 (also referred to as Asn297 or N297) is a residue at position 297 in the human antibody IgG1 which incidentally is the position at which the Fc region is glycosylated. The removal of the glycosylation ablates FcγRIIIa binding, leading to a loss of ADCC activity.

By "Fab" or "Fab region" as used herein is meant the polypeptide that comprises the VH, CH1, VL, and CL immunoglobulin domains. Fab may refer to this region in isolation, or this region in the context of a full length antibody or antibody fragment.

By "Fv" or "Fv fragment" or "Fv region" as used herein is meant a polypeptide that comprises the VL and VH domains of a single antibody. As will be appreciated by those in the art, these are made up of two domains, a variable heavy domain and a variable light domain.

By "single chain Fv" or "scFv" herein is meant a variable heavy domain covalently attached to a variable light domain, generally using a scFv linker as discussed herein, to form a scFv or scFv domain. A scFv domain can be in either orientation from N- to C-terminus (vh-linker-vl or vl-linker-vh). In general, the linker is a scFv linker as is generally known in the art, and discussed above.

By "IgG subclass modification" or "isotype modification" as used herein is meant an amino acid modification that converts one amino acid of one IgG isotype to the corresponding amino acid in a different, aligned IgG isotype. For example, because IgG1 comprises a tyrosine and IgG2 a phenylalanine at EU position 296, a F296Y substitution in IgG2 is considered an IgG subclass modification. Similarly, because IgG1 has a proline at position 241 and IgG4 has a serine there, an IgG4 molecule with a S241P is considered an IgG subclass modification. Note that subclass modifications are considered amino acid substitutions herein.

By "non-naturally occurring modification" as used herein is meant an amino acid modification that is not isotypic. For example, because none of the IgGs comprise an asparagine at position 297, the substitution N297A in IgG1, IgG2, IgG3, or IgG4 (or hybrids thereof) is considered a non-naturally occurring modification.

By "amino acid" and "amino acid identity" as used herein is meant one of the 20 naturally occurring amino acids that are coded for by DNA and RNA.

By "effector function" as used herein is meant a biochemical event that results from the interaction of an antibody Fc region with an Fc receptor or ligand. Effector functions include but are not limited to ADCC, ADCP, and CDC.

By "parent polypeptide" as used herein is meant a starting polypeptide that is subsequently modified to generate a variant. The parent polypeptide may be a naturally occurring polypeptide, or a variant or engineered version of a naturally occurring polypeptide. Parent polypeptide may refer to the polypeptide itself, compositions that comprise the parent polypeptide, or the amino acid sequence that encodes it. Accordingly, by "parent immunoglobulin" as used herein is meant an unmodified immunoglobulin polypeptide that is modified to generate a variant, and by "parent antibody" as used herein is meant an unmodified antibody that is modified to generate a variant antibody. It should be noted that "parent antibody" includes known commercial, recombinantly produced antibodies as outlined below.

By "Fc" or "Fc region" or "Fc domain" as used herein is meant the polypeptide comprising the constant region of an antibody excluding the first constant region immunoglobulin domain (e.g., CH1) and in some cases, part of the hinge. For IgG, the Fc domain comprises immunoglobulin domains CH2 and CH3 (Cγ2 and Cγ3) and the lower hinge region between CH1 (Cγ1) and CH2 (Cγ2). Although the boundaries of the Fc region may vary, the human IgG heavy chain Fc region is usually defined to include residues C226 or P230 to its carboxyl-terminus, wherein the numbering is according to the EU index as in Kabat. Accordingly, "CH" domains in the context of IgG are as follows: "CH1" refers to positions 118-215 according to the EU index as in Kabat. "Hinge" refers to positions 216-230 according to the EU index as in Kabat. "CH2" refers to positions 231-340 according to the EU index as in Kabat, and "CH3" refers to positions 341-447 according to the EU index as in Kabat. Thus, the "Fc domain" includes the —CH2-CH3 domain, and optionally a hinge domain (hinge-CH2-CH3). In some embodiments, as is more fully described below, amino acid modifications are made to the Fc region, for example to alter binding to one or more FcγR receptors or to the FcRn receptor.

By "Fc gamma receptor", "FcγR" or "FcgammaR" as used herein is meant any member of the family of proteins that bind the IgG antibody Fc region and is encoded by an FcγR gene. In humans this family includes but is not limited to FcγRI (CD64), including isoforms FcγRIa, FcγRIb, and FcγRIc; FcγRII (CD32), including isoforms FcγRIIa (including allotypes H131 and R131), FcγRIIb (including FcγRIIb-1 and FcγRIIb-2), and FcγRIIc; and FcγRIII (CD16), including isoforms FcγRIIIa (including allotypes V158 and F158) and FcγRIIIb (including allotypes FcγRIIb-NA1 and FcγRIIb-NA2) (Jefferis et al., 2002, Immunol Lett 82:57-65, entirely incorporated by reference), as well as any undiscovered human FcγRs or FcγR isoforms or allotypes. In some cases, as outlined herein, binding to one or more of the FcγR receptors is reduced or ablated. For example, reducing binding to FcγRIIIa reduces ADCC, and in some cases, reducing binding to FcγRIIIa and FcγRIIb is desired.

By "FcRn" or "neonatal Fc Receptor" as used herein is meant a protein that binds the IgG antibody Fc region and is encoded at least in part by an FcRn gene. The FcRn may be from any organism, including but not limited to humans, mice, rats, rabbits, and monkeys. As is known in the art, the functional FcRn protein comprises two polypeptides, often referred to as the heavy chain and light chain. The light chain is beta-2-microglobulin and the heavy chain is encoded by the FcRn gene. Unless otherwise noted herein, FcRn or an FcRn protein refers to the complex of FcRn heavy chain with beta-2-microglobulin. As discussed herein, binding to the FcRn receptor is desirable, and in some cases, Fc variants can be introduced to increase binding to the FcRn receptor.

By "heavy constant region" herein is meant the CH1-hinge-CH2-CH3 portion of a human IgG antibody. A number of suitable heavy constant regions are shown in FIG. 10.

By "light constant region" is meant the CL domain from kappa or lambda, the sequences of which are shown in FIG. 10.

By "position" as used herein is meant a location in the sequence of a protein. Positions may be numbered sequentially, or according to an established format, for example the EU index for antibody numbering.

By "target antigen" as used herein is meant the molecule that is bound specifically by the variable region of a given antibody. In the present case, the target antigen of interest herein is CD38 protein, usually human CD38 and optionally cynomolgus CD38, as defined below. Thus, an "anti-CD38 binding domain" is an antigen binding domain (ABD) where the antigen is CD38.

By "target cell" as used herein is meant a cell that expresses a target antigen.

By "variable domain" as used herein is meant the region of an immunoglobulin that comprises one or more Ig domains substantially encoded by any of the Vκ (V.kappa), Vλ (V.lamda), and/or VH genes that make up the kappa, lambda, and heavy chain immunoglobulin genetic loci respectively. Thus a "variable heavy domain" comprises (VH)FR1-vhCDR1-(VH)FR2-vhCDR2-(VH)FR3-vhCDR3-(VH)FR4 and a "variable light domain" comprises (VL)FR1-vlCDR1-(VL)FR2-vlCDR2-(VL)FR3-vlCDR3-(VL)FR4.

By "wild type or WT" herein is meant an amino acid sequence or a nucleotide sequence that is found in nature, including allelic variations. A WT protein has an amino acid sequence or a nucleotide sequence that has not been intentionally modified.

The antibodies of the present invention are generally isolated or recombinant. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities. "Recombinant" means the antibodies are generated using recombinant nucleic acid techniques in exogeneous host cells.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

The term "Kassoc" or "Ka", as used herein, is intended to refer to the association rate of a particular antibody-antigen interaction, whereas the term "Kdis" or "Kd," as used herein, is intended to refer to the dissociation rate of a particular antibody-antigen interaction. The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art. In some embodiments, the method for determining the $K_D$ of an antibody is by using surface plasmon resonance, for example, by using a biosensor system such as a BIACORE® system. In some embodiments, the $K_D$ of an antibody is determined by Bio-Layer Interferometry. In some embodiments, the $K_D$ is measured using flow cytometry with antigen-expressing cells. In some embodiments, the $K_D$ value is measured with the antigen immobilized. In other embodiments, the $K_D$ value is measured with the antibody (e.g., parent mouse antibody, chimeric antibody, or humanized antibody variants) immobilized. In certain embodiments, the $K_D$ value is measured in a bivalent binding mode. In other embodiments, the $K_D$ value is measured in a monovalent binding mode. Specific binding for a particular antigen or an epitope can be exhibited, for example, by an antibody having a $K_D$ for an antigen or epitope of at least about $10^{-7}$ M, at least about $10^{-8}$ M, at least about $10^{-9}$ M, at least about $10^{-10}$ M, at least about $10^{-11}$ M, at least about $10^{-12}$ M, at least about $10^{-13}$ M, at least about $10^{-14}$ M. Typically, an antibody that specifically binds an antigen will have a $K_D$ that is 20-, 50-, 100-, 500-, 1000-, 5,000-, 10,000- or more times greater for a control molecule relative to the antigen or epitope.

"Percent (%) amino acid sequence identity" with respect to a protein sequence is defined as the percentage of amino acid residues in a candidate sequence that are identical with the amino acid residues in the specific (parental) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. One particular program is the ALIGN-2 program outlined at paragraphs [0279] to [0280] of US Pub. No. 20160244525, hereby incorporated by reference. Another approximate alignment for nucleic acid sequences is provided by the local homology algorithm of Smith and Waterman, Advances in Applied Mathematics, 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986).

An example of an implementation of this algorithm to determine percent identity of a sequence is provided by the Genetics Computer Group (Madison, WI) in the "BestFit" utility application. The default parameters for this method are described in the Wisconsin Sequence Analysis Package Program Manual, Version 8 (1995) (available from Genetics Computer Group, Madison, WI). Another method of establishing percent identity in the context of the present invention is to use the MPSRCH package of programs copyrighted by the University of Edinburgh, developed by John F. Collins and Shane S. Sturrok, and distributed by Intelli-Genetics, Inc. (Mountain View, CA). From this suite of packages, the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the internet address located by placing http:// in front of blast.ncbi.nlm.nih.gov/Blast.cgi.

The degree of identity between an amino acid sequence of the present invention ("invention sequence") and the parental amino acid sequence is calculated as the number of exact matches in an alignment of the two sequences, divided by the length of the "invention sequence," or the length of the parental sequence, whichever is the shortest. The result is expressed in percent identity.

The terms "treatment", "treating", "treat", and the like, refer to obtaining a desired pharmacologic and/or physiologic effect. The effect may be prophylactic in terms of completely or partially preventing a disease or symptom thereof or reducing the likelihood of a disease or symptom thereof and/or may be therapeutic in terms of a partial or complete cure for a disease and/or adverse effect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development or progression; and (c) relieving the disease, i.e., causing regression of the disease and/or relieving one or more disease symptoms. "Treatment" is also meant to encompass delivery of an agent in order to provide for a pharmacologic effect, even in the absence of a disease or condition. For example, "treatment" encompasses delivery of a composition that can elicit an immune response or confer immunity in the absence of a disease condition, e.g., in the case of a vaccine.

An "effective amount" or "therapeutically effective amount" of a composition includes that amount of the composition which is sufficient to provide a beneficial effect to the subject to which the composition is administered. An "effective amount" of a delivery vehicle includes that amount sufficient to effectively bind or deliver a composition.

The term "nucleic acid" includes RNA or DNA molecules having more than one nucleotide in any form including single-stranded, double-stranded, oligonucleotide or polynucleotide. The term "nucleotide sequence" includes the ordering of nucleotides in an oligonucleotide or polynucleotide in a single-stranded form of nucleic acid.

The term "promoter" as used herein includes a DNA sequence operably linked to a nucleic acid sequence to be transcribed such as a nucleic acid sequence encoding a desired molecule. A promoter is generally positioned upstream of a nucleic acid sequence to be transcribed and provides a site for specific binding by RNA polymerase and other transcription factors.

A "vector" is capable of transferring gene sequences to a target cell. Typically, "vector construct," "expression vector," and "gene transfer vector," mean any nucleic acid construct capable of directing the expression of a gene of interest and which can transfer a gene sequence to a target cell, which can be accomplished by genomic integration of all or a portion of the vector, or transient or inheritable maintenance of the vector as an extrachromosomal element. Thus, the term includes cloning, and expression vehicles, as well as integrating vectors.

The term "regulatory element" as used herein includes a nucleotide sequence which controls some aspect of the expression of a nucleic acid sequence. Examples of regulatory elements illustratively include an enhancer, an internal ribosome entry site (IRES), an intron, an origin of replication, a polyadenylation signal (pA), a promoter, an enhancer, a transcription termination sequence, and an upstream regulatory domain, which contribute to the replication, transcription, and/or post-transcriptional processing of a nucleic acid sequence. In cases, regulatory elements can also include cis-regulatory DNA elements as well as transposable elements (TEs). Those of ordinary skill in the art are capable of selecting and using these and other regulatory elements in an expression construct with no more than routine experimentation. Expression constructs can be generated using a genetic recombinant approach or synthetically using well-known methodology.

A "control element" or "control sequence" is a nucleotide sequence involved in an interaction of molecules contributing to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter.

C. CD38 Protein and Anti-CD38 Binding Domains

1. CD38 Protein

The present invention provides anti-CD38 binding domains that specifically bind human and cynomolgus CD38 proteins. The amino acid sequences of human and cynomolgus CD38 proteins are shown in RefSeq accession identifiers NP_001766.2 (SEQ ID NO:28) and NP_001274206.1 (SEQ ID NO:30) respectively, with the ECD sequences (SEQ ID NO:29 and SEQ ID NO:31, respectively) shown in FIG. 7.

Accordingly, as used herein, the term "CD38" or "CD38 protein" or "CD38 polypeptide" may optionally include any such protein, variants, conjugates, or fragments thereof, including but not limited to known or wildtype CD38, as described herein, as well as any naturally occurring splice variants, amino acid variants or isoforms, and in particular the extracellular domain (ECD) fragment of CD38. That is, the ABDs of the invention generally bind to the ECD domains of both human and cyno CD38 proteins.

2. Anti-CD38 Binding Domains

The invention provides a number of anti-CD38 binding domains in different formats or orientations. Specific CDRs of anti-CD38 binding domains are described below. As discussed above, the exact numbering and placement of the CDRs can be different among different numbering systems. However, it should be understood that the disclosure of a heavy variable and/or light variable region includes the disclosure of the associated (inherent) CDRs. Accordingly, the disclosure of each heavy variable region is a disclosure of the vhCDRs (e.g. vhCDR1, vhCDR2 and vhCDR3) and the disclosure of each light variable region is a disclosure of the vlCDRs (e.g. vlCDR1, vlCDR2 and vlCDR3).

The present disclosure provides novel anti-CD38 binding domains. Such antigen binding domains can bind human and cynomolgus CD38 proteins. FIG. 6A-6G depicts the amino acid sequences of four different anti-CD38 ABDs that can bind to both human and cynomolgus CD38. In some embodiments, the heavy chain variable region and the light chain variable region are arranged in a Fab format, which, as discussed below, are optionally included into full length antibodies. In some embodiments, the heavy chain variable region and the light chain variable region are fused together to form an scFv as generally outlined herein.

Also included herein are anti-CD38 ABDs that have amino acid modifications in one or more of the CDRs and/or the framework regions.

As outlined herein, in some embodiments the set of 6 CDRs can have from 0, 1, 2, 3, 4, 5 or 6 amino acid modifications (with amino acid substitutions finding particular use). That is, the CDRs can have amino acid modifications (e.g. from 1, 2, 3, 4, 5 or 6 amino acid modifications in the set of CDRs (that is, the CDRs can be modified as long as the total number of changes in the set of 6 CDRs is less than 6 amino acid modifications, with any combination of CDRs being changed; e.g. there may be one change in vlCDR1, two in vhCDR2, none in vhCDR3, etc.). In some embodiments, amino acid substitutions in the vhCDR3 are less preferred or are avoided. In some cases, the binding affinity for either or both of human and cyno CD38 may be increased, while in other embodiments the binding affinity may be reduced. In these embodiments, binding to human and cyno CD38 is retained. Suitable assays for testing whether an anti-CD38 antigen binding domain that contains modifications as compared to the VH and VL sequences outlined herein are known in the art, such as Biacore assays or the binding assay outlined in Examples 1, 2 or 3.

In some embodiments, the anti-CD38 ABDs outlined herein may also have amino acid modifications (again, with amino acid substitutions finding particular use) in the framework regions of either or both of the variable heavy and variable light framework regions, as long as the frameworks (excluding the CDRs) retain at least about 80, 85 or 90% identity to a human germline sequence. Thus, for example, the identical CDRs as described herein can be combined with different framework sequences from human germline sequences, as long as the framework regions retain at least 80, 85 or 90% identity to a human germline sequence.

In another aspect, the invention further provides anti-CD38 binding domains that include variants of the above listed heavy chain variable and light chain variable regions. The heavy chain variable regions can be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to "VH" sequences herein, and/or contain from 1, 2, 3, 4, 5, 6, 7, 8, 9, 10 amino acid changes. The light chain variable regions can be at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to "VL" sequences herein, and/or contain from 1, 2, 3, 4, 5, 6, 7, 8, 9, 10 amino acid changes. In these embodiments, the invention includes these variants as long as the antigen binding domains still bind to human and cynomolgus CD38. Suitable assays for testing whether an anti-CD38 antigen binding domain that contains mutations as compared to the VH and VL sequences outlined herein are known in the art, such as Biacore assays and those of Examples 1, 2 and 3.

In some embodiments, the anti-CD38 binding domain is CD38TM1 and includes a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:9 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:13.

In some embodiments, the anti-CD38 binding domain is CD38TM1 and includes a vhCDR1 comprising SEQ ID NO:10, a vhCDR2 comprising SEQ ID NO:11, a vhCDR3 comprising SEQ ID NO:12, a vlCDR1 comprising SEQ ID NO:14, a vlCDR2 comprising SEQ ID NO:15, and a vlCDR3 comprising SEQ ID NO:16. In some embodiments, one or more of such 6 CDRs have from 1, 2, 3, 4 or 5 amino acid modifications. In further embodiments, any single CDR contains no more than 1 or 2 amino acid substitutions, and the modified anti-CD38 antigen binding domain retain binding to human and/or cynomolgus CD38.

In some embodiments the anti-CD38 binding domain of CD38TM1 has a VH domain that has no more than 1, 2, 3, 4 or 5 amino acid changes in SEQ ID NO:9.

In some embodiments the anti-CD38 binding domain of CD38TM1 has a VL domain that has no more than 1, 2, 3, 4 or 5 amino acid changes in SEQ ID NO:13.

In some embodiments the anti-CD38 binding domain of CD38TM1 has a VH domain that has no more than 1, 2, 3, 4 or 5 amino acid changes in SEQ ID NO:9 and a VL domain that has no more than 1, 2, 3, 4 or 5 amino acid changes in SEQ ID NO:13.

In some embodiments the anti-CD38 binding domain is CD38TM1 and has a VH with SEQ ID NO:9 and a VL with SEQ ID NO:13.

In some embodiments, the anti-CD38 binding domain is CD38TM2 and includes a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:17 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:21.

In some embodiments, the anti-CD38 binding domain is CD38TM2 and includes a vhCDR1 comprising SEQ ID NO:18, a vhCDR2 comprising SEQ ID NO:19, a vhCDR3 comprising SEQ ID NO:20, a vlCDR1 comprising SEQ ID NO:22, a vlCDR2 comprising SEQ ID NO:23, and a vlCDR3 comprising SEQ ID NO:24. In some embodiments, one or more of such 6 CDRs have from 1, 2, 3, 4 or 5 amino acid modifications. In further embodiments, a single CDR contains no more than 1 or 2 amino acid substitutions, and the modified anti-CD38 antigen binding domain retain binding to human and/or cynomolgus CD38.

In some embodiments the anti-CD38 binding domain of CD38TM2 has a VH domain that has no more than 1, 2, 3, 4 or 5 amino acid changes in SEQ ID NO:17.

In some embodiments the anti-CD38 binding domain of CD38TM1 has a VL domain that has no more than 1, 2, 3, 4 or 5 amino acid changes in SEQ ID NO:21.

In some embodiments the anti-CD38 binding domain of CD38TM2 has a VH domain that has no more than 1, 2, 3, 4 or 5 amino acid changes in SEQ ID NO:17 and a VL domain that has no more than 1, 2, 3, 4 or 5 amino acid changes in SEQ ID NO:21.

In some embodiments the anti-CD38 binding domain is CD38TM2 and has a VH with SEQ ID NO:17 and a VL with SEQ ID NO:21.

In some embodiments, the anti-CD38 binding domain is CD38TM3 and includes a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:5.

In some embodiments, the anti-CD38 binding domain is CD38TM3 and includes a vhCDR1 comprising SEQ ID NO:2, a vhCDR2 comprising SEQ ID NO:3, a vhCDR3 comprising SEQ ID NO:4, a vlCDR1 comprising SEQ ID NO:6, a vlCDR2 comprising SEQ ID NO:7, and a vlCDR3 comprising SEQ ID NO:8. In some embodiments, one or more of such 6 CDRs have from 1, 2, 3, 4 or 5 amino acid modifications. In further embodiments, a single CDR contains 1 or 2 amino acid substitutions, and the modified anti-CD38 antigen binding domain retain binding to human and/or cynomolgus CD38.

In some embodiments the anti-CD38 binding domain of CD38TM3 has a VH domain that has no more than 1, 2, 3, 4 or 5 amino acid changes in SEQ ID NO:1.

In some embodiments the anti-CD38 binding domain of CD38TM3 has a VL domain that has no more than 1, 2, 3, 4 or 5 amino acid changes in SEQ ID NO:5.

In some embodiments the anti-CD38 binding domain of CD38TM3 has a VH domain that has no more than 1, 2, 3, 4 or 5 amino acid changes in SEQ ID NO:1 and a VL domain that has no more than 1, 2, 3, 4 or 5 amino acid changes in SEQ ID NO:5.

In some embodiments the anti-CD38 binding domain is CD38TM3 and has a VH with SEQ ID NO:1 and a VL with SEQ ID NO:5.

In some embodiments, the anti-CD38 binding domain is CD38TM4 in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:1 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:25.

In some embodiments, the anti-CD38 binding domain is CD38TM4 and includes a vhCDR1 comprising SEQ ID NO:2, a vhCDR2 comprising SEQ ID NO:3, a vhCDR3 comprising SEQ ID NO:4, a vlCDR1 comprising SEQ ID NO:6, a vlCDR2 comprising SEQ ID NO:7, and a vlCDR3 comprising SEQ ID NO:8. In some embodiments, one or more of such 6 CDRs have from 1, 2, 3, 4 or 5 amino acid modifications. In further embodiments, a single CDR contains 1 or 2 amino acid substitutions, and the modified anti-CD38 antigen binding domain retain binding to human and/or cynomolgus CD38.

In some embodiments the anti-CD38 binding domain of CD38TM4 has a VH domain that has no more than 1, 2, 3, 4 or 5 amino acid changes in SEQ ID NO:1.

In some embodiments the anti-CD38 binding domain of CD38TM1 has a VL domain that has no more than 1, 2, 3, 4 or 5 amino acid changes in SEQ ID NO:25.

In some embodiments the anti-CD38 binding domain of CD38TM4 has a VH domain that has no more than 1, 2, 3, 4 or 5 amino acid changes in SEQ ID NO:1 and a VL domain that has no more than 1, 2, 3, 4 or 5 amino acid changes in SEQ ID NO:25.

In some embodiments the anti-CD38 binding domain is CD38TM4 and has a VH with SEQ ID NO:1 and a VL with SEQ ID NO:25.

In some embodiments, the anti-CD38 binding domain is CD38TM5 in the present disclosure include a heavy chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:53 and a light chain variable region having an amino acid sequence at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, or 100%) identical to SEQ ID NO:57.

In some embodiments, the anti-CD38 binding domain is CD38TM5 and includes a vhCDR1 comprising SEQ ID NO:54, a vhCDR2 comprising SEQ ID NO:55, a vhCDR3 comprising SEQ ID NO:56, a vlCDR1 comprising SEQ ID NO:58, a vlCDR2 comprising SEQ ID NO:59, and a vlCDR3 comprising SEQ ID NO:60. In some embodiments, one or more of such 6 CDRs have from 1, 2, 3, 4 or 5 amino acid modifications. In further embodiments, a single CDR contains 1 or 2 amino acid substitutions, and the modified anti-CD38 antigen binding domain retain binding to human and/or cynomolgus CD38.

In some embodiments the anti-CD38 binding domain of CD38TM5 has a VH domain that has no more than 1, 2, 3, 4 or 5 amino acid changes in SEQ ID NO:53.

In some embodiments the anti-CD38 binding domain of CD38TM5 has a VL domain that has no more than 1, 2, 3, 4 or 5 amino acid changes in SEQ ID NO:57.

In some embodiments the anti-CD38 binding domain of CD38TM5 has a VH domain that has no more than 1, 2, 3, 4 or 5 amino acid changes in SEQ ID NO:53 and a VL domain that has no more than 1, 2, 3, 4 or 5 amino acid changes in SEQ ID NO:57.

In some embodiments the anti-CD38 binding domain is CD38TM5 and has a VH with SEQ ID NO:53 and a VL with SEQ ID NO:57.

In addition to the sequence variants described herein in the heavy chain and light chain variable regions and/or CDRs for each anti-CD38 binding domain, changes in the framework region(s) of the heavy and/or light variable region(s) can be made. In some embodiments, variations are made in the framework regions that retain at least 80, 85, 90 or 95% identity to the framework region sequences described in Table 1, while keeping 6 CDRs unchanged and retaining the binding to human and/or cynomolgus CD38.

In some embodiments, variations are made in both the framework regions and the 6 CDRs while retaining the binding of the anti-CD38 binding domains to human and/or cynomolgus CD38. In these embodiments, the CDRs can have amino acid modifications (e.g., from 1, 2, 3, 4 or 5 amino acid modifications in the set of 6 CDRs, that is, the CDRs can be modified as long as the total number of changes in the set of 6 CDRs is less than 6 amino acid modifications, with any combination of CDRs being changed; e.g., there may be one change in vlCDR1, two in vhCDR2, none in vhCDR3, etc.).

Epitopes of the anti-CD38 binding domains are mapped as outlined below. The present invention not only includes the enumerated antigen binding domains and antibodies herein, but also those that compete for binding with the epitopes bound by the enumerated antigen binding domains, e.g. CD38TM1, CD38TM2, CD38TM3, CD38TM4 and CD38TM5. Antigen binding domains that recognize the same epitope can be verified in a simple competitive immunoassay showing the ability of one antigen binding domain (or an antibody containing such antigen binding domain) to block the binding of another antigen binding domain (or an antibody containing such antigen binding domain) to the target antigen CD38, for example "binning." Competitive binding studies can be done as is known in the art, generally using SPR/Biacore® binding assays, as well as ELISA and cell-based assays.

D. Characteristics of Anti-CD38 Binding Domains

The present invention provides novel anti-CD38 binding domains. The anti-CD38 binding domains specifically bind to human and cynomolgus CD38, and preferably the ECD of the human and cynomolgus CD38. Binding to both human and cynomologous CD38 is useful because cynomolgous animals may be used as a model for human subjects to help determine, estimate, and understand the in vivo effects and behavior of the CD38-targeting molecule, such as, e.g., regarding pharmacokinetics, pharmacodynamics, and toxicology; wherein the model may have target binding and target cell killing by the molecule which is translatable to a related species.

In some embodiments, the anti-CD38 binding domains described herein bind to human and cynomolgus CD38 with high affinities. The $K_D$ value can be measured with the antigen immobilized or with the antibody immobilized. The $K_D$ value can also be measured in a monovalent or a bivalent binding mode. For example, when formatted into IgG1 and measured by flow cytometry, the $K_D$ values of the antigen binding domains binding to human CD38 can be $1 \times 10^{-6}$M or less, $5 \times 10^{-7}$M or less, $2.5 \times 10^{-7}$M or less, $1 \times 10^{-7}$M or less, $5 \times 10^{-8}$M or less, $1 \times 10^{-8}$M or less, $1 \times 10^{-9}$M or less, or $1 \times 10^{-10}$M or less. The $K_D$ values of the antigen binding domains binding to cynomolgus CD38 can be $1 \times 10^{-6}$M or less, $5 \times 10^{-7}$M or less, $2.5 \times 10^{-7}$M or less, $1 \times 10^{-7}$M or less, $5 \times 10^{-8}$M or less, $2.5 \times 10^{-8}$M or less, $1 \times 10^{-8}$M or less, $5 \times 10^{-9}$M or less, $1 \times 10^{-9}$M or less, $5 \times 10^{-10}$M or less, or $1 \times 10^{-10}$M or less. In some embodiments, the $K_D$ values of the antigen binding domains binding to human CD38 range from 0.1 nM-1 µM, 0.25 nM-500 nM, 0.5 nM 250 nM, 1 nM-100 nM M, or 1.5 nM-50 nM. In some embodiments, the $K_D$ values of the antigen binding domains binding to cynomolgus CD38 range from 0.1 nM-1 µM, 0.25 nM-500 nM, 0.5 nM-250 nM, 1 nM-100 nM M, or 2 nM-50 nM.

Furthermore, the anti-CD38 binding domains provided in this disclosure can bind to various amino acids in the epitope on human CD38 ECD. In some embodiments, the anti-CD38 binding domains bind to R78 and/or D81. In some embodiments, the anti-CD38 binding domains bind to F216, L262, L124, C201, L230, C254, and/or 5274. In some embodiments, the anti-CD38 binding domains described herein bind to an epitope on CD38 non-overlapping with daratumumab. In some embodiments, the anti-CD38 binding domains described herein bind to an epitope on CD38 partially overlapping with daratumumab. In some embodiments, the anti-CD38 binding domains described herein are able to bind to human and/or cynomolgus CD38 in the presence of daratumumab.

In some embodiments, one or more of the anti-CD38 binding domains disclosed herein are included in a composition, such as in an antibody, which can be used to induce complement-dependent cytotoxicity (CDC) and antibody-dependent cellular cytotoxicity (ADCC) in cells with increased expression of CD38, such as multiple myeloma cells.

E. Compositions of Anti-CD38 Binding Domains

As outlined herein, the anti-CD38 binding domains of the invention can be used in different formats, for example as scFvs or as Fabs included into traditional tetrameric antibodies.

1. scFvs Comprising Anti-CD38 Binding Domains

In some embodiments, the composition comprises an scFv that includes an anti-CD38 binding domain described herein. The scFvs binds to human and cynomolgus CD38, and comprises a heavy chain variable region (VH) and a light chain variable region (VL) linked by an scFv linker. The VL and VH can be in either orientation, e.g. from N- to C-terminus "VH-scFv linker-VL" or "VL-scFv linker-VH".

While any suitable linker can be used, many embodiments utilize a glycine-serine polymer, including for example the 15-residue (Gly4Ser)$_3$ peptide (SEQ ID NO:32). Suitable scFv linkers which may be used in forming non-covalent multivalent structures include, for example, GGS (SEQ ID NO:33), GGGS (SEQ ID NO:34), GGGGS (SEQ ID NO:35), GGGGSGGG (SEQ ID NO:36), GGSGGGG (SEQ ID NO:37), as well as GSTSGGGSGGGSGGGSS (SEQ ID NO:38) or any peptide sequence that allows for recombinant attachment of the heavy chain variable region and light chain variable region with sufficient length and flexibility to allow each domain to retain its biological function.

Linkers of variable length can be used in this invention. In some embodiments, linkers of 1 to 50 amino acids in length is used. In some embodiments, linkers of 3 to 12 amino acids in length is used, and the resulting scFv monomers tend to form multimers or oligomers (e.g. diabodies, triabodies, and tetrabodies) due to self-association, with the majority form being dimers. In some embodiments, linkers of 5 amino acids in length, such as GGGGS (SEQ ID NO:35), is used, and diabodies can be formed from the ABDs. In some embodiments, linkers of longer than 12 (e.g., 13, 14, 15, 16, 17, 18, 19, or 20) amino acids in length is used, and the resulting scFv predominantly forms monomers with only a minority fraction undergoing spontaneous multimerization. In some embodiments, linkers of 1 to 3 amino acids are used, which promote multimerization of scFv to higher order structures larger than dimeric forms, such as trimers and/or mixtures of trimers and tetramers.

Multimerization of scFvs is also included in the present invention. It may be controlled by molecular engineering strategies which are either covalent or non-covalent, e.g., covalent strategies involving single-chain tandem arrangements, covalent strategies involving cysteine-mediated, disulfide bond stabilized multimers, and/or non-covalent strategies involving dimerization domains, linker choice, and/or variable domain order. Multiple strategies (e.g., linker-related non-covalent multimerization and covalent disulfide bond stabilization) may be combined to generate scFv multimers (see e.g. Lu D et al., J Immunol Methods 279: 219-32 (2003)).

In some embodiments, the invention provides ABDs that comprise the variable heavy and variable light domains, including the VH and VL domains selected from the group consisting of those of CD38TM1, CD38TM2, CD38TM3, CD38TM4, CD38TM5 and CD38TM6. In some embodiments, the ABDs are in the format of scFv. The VH and VL domains are linked by a 5 amino acid scFv linker, such as GGGGS (SEQ ID NO:35) to form from N- to C-terminus "VH-scFv linker-VL" or "VL-scFv linker-VH". Diabodies can be formed from such ABDs. An illustration of the X-ray structure of an exemplary scFv is presented in FIG. 12. This scFv contains a VH and VL from CD38TM4 and a scFv linker GGGGS (SEQ ID NO:35), and forms the diabody structure.

2. Antibodies Comprising an Anti-CD38 Binding Domain

In some embodiments, the compositions of the invention are traditional, tetrameric antibodies that comprise the variable heavy and variable light domains of the invention that form ABDs, including CD38TM1, CD38TM2, CD38TM3, CD38TM4, CD38TM5 and CD38TM6. In general, these VH and VL pairs are added to the heavy chain constant domains (CH1-hinge-CH2-CH3) of human and variant human IgG1, IgG2 and IgG4, the sequences of which are shown in FIG. 10, and the light constant domains (CL) of lambda or kappa, also shown in FIG. 10. In some embodiments, the present invention provides a composition comprises an Fab that includes an anti-CD38 binding domain described herein. The C-terminus of the heavy chain variable region (containing the vhCDR1, vhCDR2 and vhCDR3) is attached to the N-terminus of the CH1 domain of the heavy chain, and the C-terminus of the light chain variable region (containing the vlCDR1, vlCDR2 and vlCDR3) is attached to the N-terminus of the light chain constant domain. Either the constant lambda or kappa domain can be used in the invention, as well as variants of the CH1 domain and light chain constant domain described herein.

Suitable heavy chain constant domains include, but are not limited to, those depicted in FIG. 10.

In some embodiments, the antibodies comprise a heavy chain (VH-CH1-hinge-CH2-CH3) with the VH and VL of CD38TM1. In these embodiments, the constant heavy domain can be from human and variant IgG1, IgG2 and IgG4 as depicted in FIG. 10.

In some embodiments, the VH (SEQ ID NO:9) is made with a heavy constant region selected from the group consisting of SEQ ID NOs:39, 40, 41, 42, 43, 44, 45, 46, 47, 48, 49 or 50, and the VL (SEQ ID NO:13) is made with a constant light domain selected from SEQ ID NOs:51 and 52.

In some embodiments, the antibodies comprise a heavy chain (VH-CH1-hinge-CH2-CH3) with the VH and VL of CD38TM2. In these embodiments, the constant heavy domain can be from human and variant IgG1, IgG2 and IgG4 as depicted in FIG. 10.

In some embodiments, the VH (SEQ ID NO:17) is made with a heavy constant region selected from the group consisting of SEQ ID NOs:39, 40, 41, 42, 43, 44, 45, 46, 47, 48, 49 or 50, and the VL (SEQ ID NO:21) is made with a constant light domain selected from SEQ ID NOs:51 and 52.

In some embodiments, the antibodies comprise a heavy chain (VH-CH1-hinge-CH2-CH3) with the VH and VL of CD38TM3. In these embodiments, the constant heavy domain can be from human and variant IgG1, IgG2 and IgG4 as depicted in FIG. 10.

In some embodiments, the VH (SEQ ID NO:1) is made with a heavy constant region selected from the group consisting of SEQ ID NOs:39, 40, 41, 42, 43, 44, 45, 46, 47, 48, 49 or 50, and the VL (SEQ ID NO:5) is made with a constant light domain selected from SEQ ID NOs:51 and 52.

In some embodiments, the antibodies comprise a heavy chain (VH-CH1-hinge-CH2-CH3) with the VH and VL of CD38TM4. In these embodiments, the constant heavy domain can be from human and variant IgG1, IgG2 and IgG4 as depicted in FIG. 10.

In some embodiments, the VH (SEQ ID NO:1) is made with a heavy constant region selected from the group consisting of SEQ ID NOs:39, 40, 41, 42, 43, 44, 45, 46, 47, 48, 49 or 50, and the VL (SEQ ID NO:25) is made with a constant light domain selected from SEQ ID NOs:51 and 52.

In some embodiments, the antibodies comprise a heavy chain (VH-CH1-hinge-CH2-CH3) with the VH and VL of CD38TM5. In these embodiments, the constant heavy domain can be from human and variant IgG1, IgG2 and IgG4 as depicted in FIG. 10.

In some embodiments, the VH (SEQ ID NO:53) is made with a heavy constant region selected from the group consisting of SEQ ID NOs:39, 40, 41, 42, 43, 44, 45, 46, 47, 48, 49 or 50, and the VL (SEQ ID NO:57) is made with a constant light domain selected from SEQ ID NOs:51 and 52.

Additional substitutions can be introduced is the Fc region of the antibody as outlined below.

3. Inclusion in Fusion Proteins

In some embodiments, the anti-CD38 binding domains of the invention can be included in fusion proteins such as generally described in U.S. application Ser. Nos. 14/774,130, 14/965,882, 15/114,487, 15/114,474, 15/125,126, 15/125,142, and 15/317,892; and U.S. Provisional Application Nos. 62/795,633, 62/945,107 and 62/945,106, such as shown in FIG. 9.

4. Antibody Engineering

The anti-CD38 binding domains and compositions comprising such anti-CD38 binding domains can be modified, or engineered, to alter the amino acid sequences by amino acid substitutions. As discussed herein, amino acid substitutions can be made to alter the affinity of the CDRs for the protein (e.g. human and/or cynomolgus CD38, including both increasing and decreasing binding), as well as to alter additional functional properties of the antigen binding domains and antibodies.

Additionally, in some embodiments, the Fc regions of the antibodies may be engineered to include modifications, typically to alter one or more functional properties of the antibody, such as serum half-life, complement fixation, Fcγ receptor binding, and/or antigen-dependent cellular cytotoxicity. Furthermore, an antigen binding domain and an antibody according to at least some embodiments of the invention may be chemically modified (e.g., one or more chemical moieties can be attached to the antigen binding domain and to the antibody) or be modified to alter its glycosylation, or to alter one or more functional properties of the antigen binding domain and the antibody. Such embodiments are described further below. The numbering of residues in the Fc region is that of the EU index of Kabat.

In one embodiment, the hinge region is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In still another embodiment, the antibody can be modified to abrogate in vivo Fab arm exchange, in particular when IgG4 constant domains are used. Specifically, this process involves the exchange of IgG4 half-molecules (one heavy chain plus one light chain) between other IgG4 antibodies that effectively results in bispecific antibodies which are functionally monovalent. Mutations to the hinge region and constant domains of the heavy chain can abrogate this exchange (see Aalberse, RC, Schuurman J., 2002, *Immunology* 105:9-19). As outlined herein, a mutation that finds particular use in the present invention is the S241P (Kabat numbering, S228P EU numbering) in the context of an IgG4 constant domain. IgG4 finds use in the present invention as it has no significant effector function, and is thus used to block the receptor binding to its ligand without cell depletion.

In some embodiments, amino acid substitutions can be made in the Fc region, in general for altering binding to FcγR receptors. There are a number of useful Fc substitutions that can be made to alter binding to one or more of the FcγR receptors. Substitutions that result in increased binding as well as decreased binding can be useful. For example, it is known that increased binding to FcγRIIIa generally results in increased ADCC (antibody dependent cell-mediated cytotoxicity; the cell-mediated reaction wherein nonspecific cytotoxic cells that express FcγRs recognize bound antibody on a target cell and subsequently cause lysis of the target cell. Similarly, decreased binding to FcγRIIb (an inhibitory receptor) can be beneficial as well in some circumstances. Amino acid substitutions that find use in the present invention include those listed in U.S. Ser. No. 11/124,620 (particularly FIG. 41) and U.S. Pat. No. 6,737,056, both of which are expressly incorporated herein by reference in their entirety and specifically for the variants disclosed therein.

In yet another example, the Fc region is modified to increase the ability of the antibody to mediate antibody dependent cellular cytotoxicity (ADCC) and/or to increase the affinity of the antibody for an Fcγ receptor, and/or increase FcRn binding, by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L et al. (2001) *J. Biol. Chem.* 276:6591-6604). Specific mutations at positions 256, 290, 298, 333, 334 and 339 are shown to improve binding to FcγRIII. Additionally, the following combination mutants are shown to improve FcγRIII binding: T256A/S298A, S298A/E333A, S298A/K224A and S298A/E333A/K334A. Furthermore, mutations such as M252Y/S254T/T256E or M428L/N434S improve binding to FcRn and increase antibody circulation half-life (see Chan C A and Carter P J (2010) *Nature Rev Immunol* 10:301-316).

In addition, the antibodies of the invention are modified to increase its biological half-life. Various approaches are possible. For example, one or more of the following mutations can be introduced: T252L, T254S, T256F, as described in U.S. Pat. No. 6,277,375 to Ward. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Additional mutations to increase serum half-life are disclosed in U.S. Pat. Nos. 8,883,973, 6,737,056 and 7,371,826 and include 428L, 434A, 434S, and 428L/434S.

In still another embodiment, the glycosylation of an antibody is modified. For example, an aglycosylated antibody can be made (i.e., the antibody lacks glycosylation). Glycosylation can be altered to, for example, increase the affinity of the antibody for antigen or reduce effector function such as ADCC. Such carbohydrate modifications can be accomplished by, for example, altering one or more sites of glycosylation within the antibody sequence, for example N297. For example, one or more amino acid substitutions can be made that result in elimination of one or more variable region framework glycosylation sites to thereby eliminate glycosylation at that site, with an alanine replacement finding use in some embodiments.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. See for example, U.S. Patent Publication No. 20040110704 and WO 2003/035835.

Another modification of the antibodies herein that is contemplated by the invention is PEGylation or the addition of other water soluble moieties, typically polymers, e.g., in order to enhance half-life. An antibody can be PEGylated to, for example, increase the biological (e.g., serum) half-life of the antibody as is known in the art.

In addition to substitutions made to alter binding affinity to FcγRs and/or FcRn and/or increase in vivo serum half-life, additional antibody modifications can be made, as described in further detail below.

In some cases, affinity maturation is done. Amino acid modifications in the CDRs are sometimes referred to as "affinity maturation". An "affinity matured" antigen binding domain or antibody is one having one or more alteration(s) in one or more CDRs which results in an improvement in the affinity of the antigen binding domain or antibody for antigen, compared to a parent which does not possess those alteration(s). In some cases, it may be desirable to decrease the affinity of an antibody to its antigen. Affinity maturation can be done to increase the binding affinity of the antigen binding domain or antibody for the antigen by at least about 10% to 50-100-150% or more, or from 1 to 5 fold as compared to the "parent" antibody. Preferred affinity matured antigen binding domains or antibodies will have nanomolar or even picomolar affinities for the antigen. Affinity matured antibodies are produced by known procedures.

In some embodiments, one or more amino acid modifications are made in one or more of the CDRs of the CD38 binding domains of the invention. In general, only 1 or 2 or 3-amino acids are substituted in any single CDR, and generally no more than from 1, 2, 3. 4, 5, 6, 7, 8 9 or 10 changes are made within a set of 6 CDRs (e.g. vhCDR1-3 and vlCDR1-3). However, it should be appreciated that any combination of no substitutions, 1, 2 or 3 substitutions in any CDR can be independently and optionally combined with any other substitution.

Alternatively, amino acid modifications can be made in one or more of the CDRs of the CD38 binding domains of the invention that are "silent", e.g. that do not significantly alter the affinity of the antigen binding domain or antibody for the antigen. These can be made for a number of reasons, including optimizing expression (as can be done for the nucleic acids encoding the antigen binding domains or antibodies of the invention).

F. Nucleic Acids Encoding Antibodies

Nucleic acid compositions encoding the anti-CD38 binding domains and compositions comprising such antigen binding domains are also provided, as well as expression vectors containing the nucleic acids and host cells transformed with the nucleic acid and/or expression vector compositions. As will be appreciated by those in the art, the protein sequences depicted herein can be encoded by any number of possible nucleic acid sequences, due to the degeneracy of the genetic code.

The nucleic acid compositions that encode the compositions comprising anti-CD38 binding domains will depend on the format of the compositions. Traditional tetrameric antibodies containing two heavy chains and two light chains are encoded by two different nucleic acids, one encoding the heavy chain and one encoding the light chain. These can be put into a single expression vector or two expression vectors, as is known in the art, transformed into host cells, where they are expressed to form the antibodies of the invention. In some embodiments, for example when scFv constructs are used, a single nucleic acid encoding the heavy variable region-linker-light variable region is generally used, which can be inserted into an expression vector for transformation into host cells. The nucleic acids can be put into expression vectors that contain the appropriate transcriptional and translational control sequences, including, but not limited to, signal and secretion sequences, regulatory sequences, promoters, origins of replication, selection genes, etc.

Preferred mammalian host cells for expressing the recombinant antibodies according to at least some embodiments of the invention include Chinese Hamster Ovary (CHO cells), PER.C6, HEK293 and others as is known in the art.

To create a scFv gene, the VH- and VL-encoding DNA fragments are operatively linked to another fragment encoding a flexible linker, e.g., encoding the amino acid sequence GGGGS and others discussed herein, such that the VH and VL sequences can be expressed as a contiguous single-chain protein, with the VL and VH regions joined by the flexible linker.

G. Formulations

The therapeutic compositions used in the practice of the foregoing methods can be formulated into pharmaceutical compositions comprising a carrier suitable for the desired delivery method. Suitable carriers include any material that when combined with the therapeutic composition retains the therapeutic function of the therapeutic composition and is generally non-reactive with the patient's immune system. Examples include, but are not limited to, any of a number of standard pharmaceutical carriers such as sterile phosphate buffered saline solutions, bacteriostatic water, and the like (see, generally, Remington's Pharmaceutical Sciences 16$^{th}$ Edition, A. Osal., Ed., 1980). Acceptable carriers, excipients, or stabilizers are nontoxic to recipients at the dosages and concentrations employed and may include buffers.

The pharmaceutical composition comprising the anti-CD38 binding domains or antibodies of the present invention may be formulated for any suitable route and means of administration, including, but not limited to intravenous infusion.

For intravenous infusion, in some embodiments, the pharmaceutical composition comprising the anti-CD38 binding domains or antibodies of the present invention is formulated in an aqueous buffer solution containing a cryogenic protectant and a surfactant. In some embodiments, the pharmaceutical composition comprising the anti-CD38 binding domains or antibodies of the present invention is formulated in an aqueous sodium citrate buffer solution containing sucrose as a cryogenic protectant and polysorbate 80 as a surfactant and is maintained at pH 4.8-5.2. In some embodiments, the pharmaceutical composition comprising the anti-CD38 binding domains or antibodies of the present invention is formulated in 20 mM sodium citrate buffer, pH 5.0, with 200 mM sucrose and 0.02% volume/volume polysorbate 80. An exemplary formulation is listed below:

| Ingredient | Amount per mL | Function |
|---|---|---|
| Composition comprising an anti-CD38 binding domain or antibody | 0.50 mg | Active Ingredient |
| Sodium Citrate, dihydrate | 3.82 mg | Buffering agent, conjugated base |
| Citric Acid, monohydrate | 1.47 mg | Buffering agent, acid |
| Sucrose | 68.4 mg | Cryogenic protectant |
| Polysorbate 80 | 0.2 mg | Surfactant stabilizer |
| Water for Injection (WFI) | q.s. to 1 mL | Solvent |
| Sodium Hydroxide | As needed to adjust to pH 4.8 to 5.2 | Base, adjust pH |
| Hydrochloric Acid | As needed to adjust to pH 4.8 to 5.2 | Acid, adjust pH |

The formulations of the pharmaceutical compositions of the invention may conveniently be presented in unit dosage form and may be prepared by any of the methods well known in the art of pharmacy. In such form, the composition is divided into unit doses containing appropriate quantities of the active component.

The dosing amounts and frequencies of administration are, in a preferred embodiment, selected to be therapeutically or prophylactically effective. As is known in the art, adjustments for protein degradation, systemic versus localized delivery, and rate of new protease synthesis, as well as the age, body weight, general health, sex, diet, time of administration, drug interaction and the severity of the condition may be necessary, and will be ascertainable with routine experimentation by those skilled in the art.

H. Methods for Using Antibodies

The anti-CD38 binding domains and composition comprising such anti-CD38 binding domains of the invention can be used in a number of diagnostic and therapeutic applications.

1. Diagnostic Uses

The anti-CD38 binding domains and composition comprising such anti-CD38 binding domains of the invention can find use in the in vitro or in vivo diagnosis of CD38-expressing cancers, including imaging of tumors that overexpress CD38.

Generally, diagnosis can be done in several ways. In one embodiment, a tissue from a patient, such as a biopsy sample, is contacted with an anti-CD38 antibody, generally labeled, such that the antibody binds to the endogenous CD38. The level of signal from the label is compared to that of normal non-cancerous tissue either from the same patient or a reference sample, to determine the presence or absence of CD38-expressing cancer. The biopsy sample can be from a solid tumor, a blood sample (for lymphomas and leukemias such as multiple myeloma, ALL, T cell lymphoma, etc). In general, in this embodiment, the anti-CD38 antibody is labeled, for example with a fluorophore or other optical label, that is detected using a fluorometer or other optical detection system as is well known in the art.

In another embodiment, a labeled secondary antibody is contacted with the sample, for example using an anti-human IgG antibody from a different mammal (mouse, rat, rabbit, goat, etc.) to form a sandwich assay as is known in the art. Alternatively, the anti-CD38 antibody could be directly labeled (i.e. biotin) and detection can be done by a secondary antibody directed to the labeling agent in the art.

Once overexpression of CD38 is seen, treatment can proceed with the administration of an anti-CD38 antigen binding domain or a composition comprising an anti-CD38 binding domain according to the invention as outlined herein.

In other embodiments, in vivo diagnosis is done. Generally, in this embodiment, the anti-CD38 antibody (including antibody fragments) is injected into the patient and imaging is done. In this embodiment, for example, the antibody is generally labeled with an optical label or an MRI label, such as a gadolinium chelate, radioactive labeling of mAb (including fragments).

Particularly useful antibodies for use in diagnosis include, but are not limited to the enumerated antibodies, or antibodies that utilize the CDRs with variant sequences, or those that compete for binding with any of the antibodies described herein.

In many embodiments, a diagnostic antibody is labeled. By "labeled" herein is meant that the antibodies disclosed herein have one or more elements, isotopes, or chemical compounds attached to enable the detection in a screen or diagnostic procedure. In general, labels fall into several classes: a) immune labels, which may be an epitope incorporated as a fusion partner that is recognized by an antibody, b) isotopic labels, which may be radioactive or heavy isotopes, c) small molecule labels, which may include fluorescent and colorimetric dyes, or molecules such as biotin that enable other labeling methods, and d) labels such as particles (including bubbles for ultrasound labeling) or paramagnetic labels that allow body imagining. Labels may be incorporated into the antibodies at any position and may be incorporated in vitro or in vivo during protein expression, as is known in the art.

Diagnosis can be done either in vivo, by administration of a diagnostic antibody that allows whole body imaging as described below, or in vitro, on samples removed from a patient. "Sample" in this context includes any number of things, including, but not limited to, bodily fluids (including, but not limited to, blood, urine, serum, lymph, saliva, anal and vaginal secretions, perspiration and semen), as well as tissue samples such as result from biopsies of relevant tissues.

In addition, as outlined below, information regarding the protein expression levels of CD38 can be used to determine which antibodies should be administered to a patient.

2. Disease Treatment

The anti-CD38 binding domains and composition comprising such anti-CD38 binding domains of the invention find particular use in treating diseases, disorders, and/or conditions which may be mediated, regulated or otherwise affected by CD38 overexpression in a subject or a human patient in need thereof. The treatment comprises administering to the subject or patient a therapeutically effective amount of a composition comprising an anti-CD38 binding domain of the invention. Among certain embodiments of the present invention is a composition comprising an anti-CD38 binding domains of the invention for the treatment or prevention of a cancer or immune disorder associated with CD38 overexpression. In some embodiments, the disease, disorder, or condition to be treated using this method of the invention is hematopoietic cancers containing CD38-overpressing cells such as multiple myeloma, and more generally, in conditions associated with loss of growth control in CD38 expressing cells. Apart from multiple myeloma, CD38 is also upregulated in many other hematopoietic malignancies and in cell lines derived from various hematopoietic malignancies, such as non-Hodgkin's lymphoma (NHL), Burkitt's lymphoma (BL), B chronic lymphocytic leukemia (B-CLL), B and T acute lymphocytic leukemia (ALL), T cell lymphoma (TCL), acute myeloid leukemia (AML), hairy cell leukemia (HCL), Hodgkin's Lymphoma (HL), and chronic myeloid leukemia (CML).

In some embodiments, the anti-CD38 binding domains and/or composition comprising such anti-CD38 binding domains of the invention are used in combination with an existing anti-CD38 antibody, e.g., daratumumab, for the treatment of a cancer or immune disorder associated with CD38 overexpression, such as multiple myeloma. In some embodiments, the anti-CD38 binding domains and/or composition comprising such anti-CD38 binding domains of the invention are used to treat patient associated with CD38 overexpression, such as a multiple myeloma patient, who has already been exposed to an anti-CD38 antibody, such as, e.g., daratumumab. In some embodiments, the anti-CD38 binding domains and/or composition comprising such anti-CD38 binding domains of the invention are used to treat patient associated with CD38 overexpression, such as a multiple myeloma patient, who has suffered failed treatment by an existing anti-CD38 antibody, e.g., daratumumab. In some embodiments, the anti-CD38 binding domains and/or composition comprising such anti-CD38 binding domains are used in combination with an existing anti-CD38 antibody for the treatment of diseases associated with CD38 overexpression, such as multiple myeloma, wherein the anti-CD38 binding domains bind to an epitope on CD38 different from the epitope bound by the existing anti-CD38 antibody.

VI. EXAMPLES

The invention now being generally described, will be more readily understood by reference to the following examples, which are included merely for purposes of illustration of certain aspects and embodiments of the present invention, and is not intended to limit the invention.

A. Example 1: Anti-CD38 Antigen Binding Clones Bind to Human and Cynomolgus CD38

1. Anti-CD38 Antigen Binding Clones Bind to Cells Expressing CD38

Anti-CD38 antigen binding clones were formatted into human IgG1 and their binding to CD38 protein was assayed. Human multiple myeloma cells MOLP-8 expressing human CD38 and cells expressing recombinant cynomolgus CD38 were incubated with an anti-CD38 antibody or a secondary antibody-only control at a 100 nM concentration. Antibody binding to CD38 was detected using a fluorophore conjugated anti-human IgG secondary antibody. Cells were then analyzed by flow cytometry, and fold-over-background (FOB) was calculated using the mean fluorescence intensity (MFI) of anti-CD38 antibody in comparison with the secondary antibody only control. Anti-CD38 binding clones bind to both human and cynomolgus CD38, and exemplary data from clones CD38TM3, CD38TM1 and CD38TM2, CD38TM5 and CD38TM6 is shown in Table 2.

TABLE 2

| Clone | Human CD38 (FOB) | Cynomolgus CD38 (FOB) |
|---|---|---|
| CD38TM3 | 212.2 | 528.2 |
| CD38TM1 | 397.1 | 1920.1 |
| CD38TM2 | 39.6 | 271.6 |
| CD38TM5 | 550.1 | 104.5 |
| CD38TM6 | 104.1 | 176.1 |

2. Anti-CD38 Antigen Binding Clones Bind to Purified CD38

Binding of anti-CD38 antigen binding clones to purified human and cynomolgus CD38 molecules was also tested. Anti-CD38 antigen binding clones were formatted into scFv, which were then fused to a Shiga toxin A subunit to generate CD38-targeting molecules. For each anti-CD38 scFv, heavy chain variable region (VH) was either fused to the N terminus or C terminus of the light chain variable region (VL) via the GGGGS linker. A reference anti-CD38 binding clone fused with Shiga toxin A subunit (CD38 Targeting Reference molecule #1-SLTA, or CD38TR1-SLTA) was also included in the test, as well as a modified anti-CD38 binding clone CD38TM4 fused to Shiga toxin A subunit, which contains amino acid substitutions in the light chain framework region of CD38TM3 to enable purification by protein L chromatography. Amino acid sequences of anti-CD38/Shiga toxin A fusion protein tested are: SEQ ID NO:40 (CD38TM1-SLTA), SEQ ID NO:41 (CD38TM2-SLTA), SEQ ID NO:42 (CD38TM3-SLTA), SEQ ID NO:43 (CD38TM4-SLTA) and SEQ ID NO:44 (CD38TR1-SLTA).

Briefly, Nunc maxisorp plates were coated with recombinant human or cynomolgus monkey CD38 in PBS overnight at 4° C. The wells were washed and blocked, and then incubated with a serial dilution of the CD38-targeting molecules. CD38-targeting molecules bound to the wells were detected by a two-step method including a murine monoclonal antibody which detects the Shiga toxin domain, and then an anti-mouse horseradish peroxidase (HRP) conjugated secondary antibody. HRP activity was detected by Ultra TMB ELISA Substrate (Thermo Fisher) and the absorbance was read at 450 nM.

Anti-CD38 antigen binding clones CD38TM1, CD38TM2, CD38TM3 and CD38TM4 bind to both human and cynomolgus CD38. In contrast, CD38TR1 only binds to human CD38. Binding of each anti-CD38 binding clone was tested in the format of an scFv fusion to a Shiga toxin A Subunit (SLTA), as shown in FIGS. 2A-3B, and FIGS. 3A-3B. CD38TM4 was expressed CD38 ECD protein with a specific mutation as a percentage of binding to wildtype CD38. Values marked in bold indicate the amino acids that are critical for binding and surface accessibility (based on published CD38 structure) of the anti-CD38 antigen binding clones.

CD38TM4 bind an epitope partially overlapping with the CD38TR1 and daratumumab on human CD38. CD38TR1 binds to the epitope including F216, L262, Q272, and F273 on human CD38. Daratumumab binds to the epitope including F274 and F275 on human CD38.

TABLE 5

| Human CD38 ECD | | CD38TM1 | CD38TM2 | CD38TM4 | CD38TM3 | CD38TR1 | Daratumamab |
|---|---|---|---|---|---|---|---|
| Amino Acid Position | Mutation | Mean % of wildtype | Mean % of wildtype | Mean % of wildtype | Mean % of wildtype | Mean % of wildtype | Mean % of wildtype |
| 78 | R78A | 2% | 3% | 106% | 130% | 80% | 52% |
| 81 | D81A | 8% | 9% | 109% | 143% | 128% | 292% |
| 119 | C119A | 108% | 108% | 12% | 26% | 83% | 85% |
| 124 | L124A | 84% | 92% | 23% | 43% | 259% | 169% |
| 201 | C201A | 90% | 58% | 4% | 5% | 130% | 109% |
| 216 | F216A | 89% | 74% | 18% | 29% | 25% | 140% |
| 230 | L230A | 72% | 111% | 7% | 19% | 17% | 64% |
| 254 | C254A | 48% | 81% | 7% | 38% | 46% | 67% |
| 262 | L262A | 68% | 97% | 12% | 32% | 33% | 83% |
| 272 | Q272A | 145% | 135% | 68% | 119% | 191% | 167% |
| 272 | Q272R | 105% | 101% | 71% | 106% | 14% | 162% |
| 273 | F273A | 157% | 117% | 89% | 135% | 10% | 197% |
| 274 | S274F | 93% | 134% | 101% | 89% | 155% | 27% |
| 274 | S274F | 150% | 124% | 80% | 139% | 74% | 14% |
| 275 | C275A | 18% | 37% | 0.3% | 17% | 14% | 18% |

Anti-CD38 antigen binding clones CD38TM1 and CD38TM2 share the same critical contact residues (1R78 and D81) on human CD38. Critical residues for CD38TM5 on human CD38 include R78, H79 and D81 (data not shown). Critical residues for CD38TM3 on human CD38 include F216, alone) for 70 minutes. Then 0.5 μg/ml of an anti-CD38/ Shiga toxin fusion molecule (~5 nM) was added and incubated with the cells for 48 hours. Antibody binding to CD38 was detected using a primary antibody recognizing Shiga toxin A subunit, and a FITC conjugated anti-IgG secondary antibody followed by flow cytometry. Mean fluorescence intensity (MFI) of anti-CD38 antigen binding clones was calculated after subtracting the signal from the secondary antibody only control.

Figure 1:
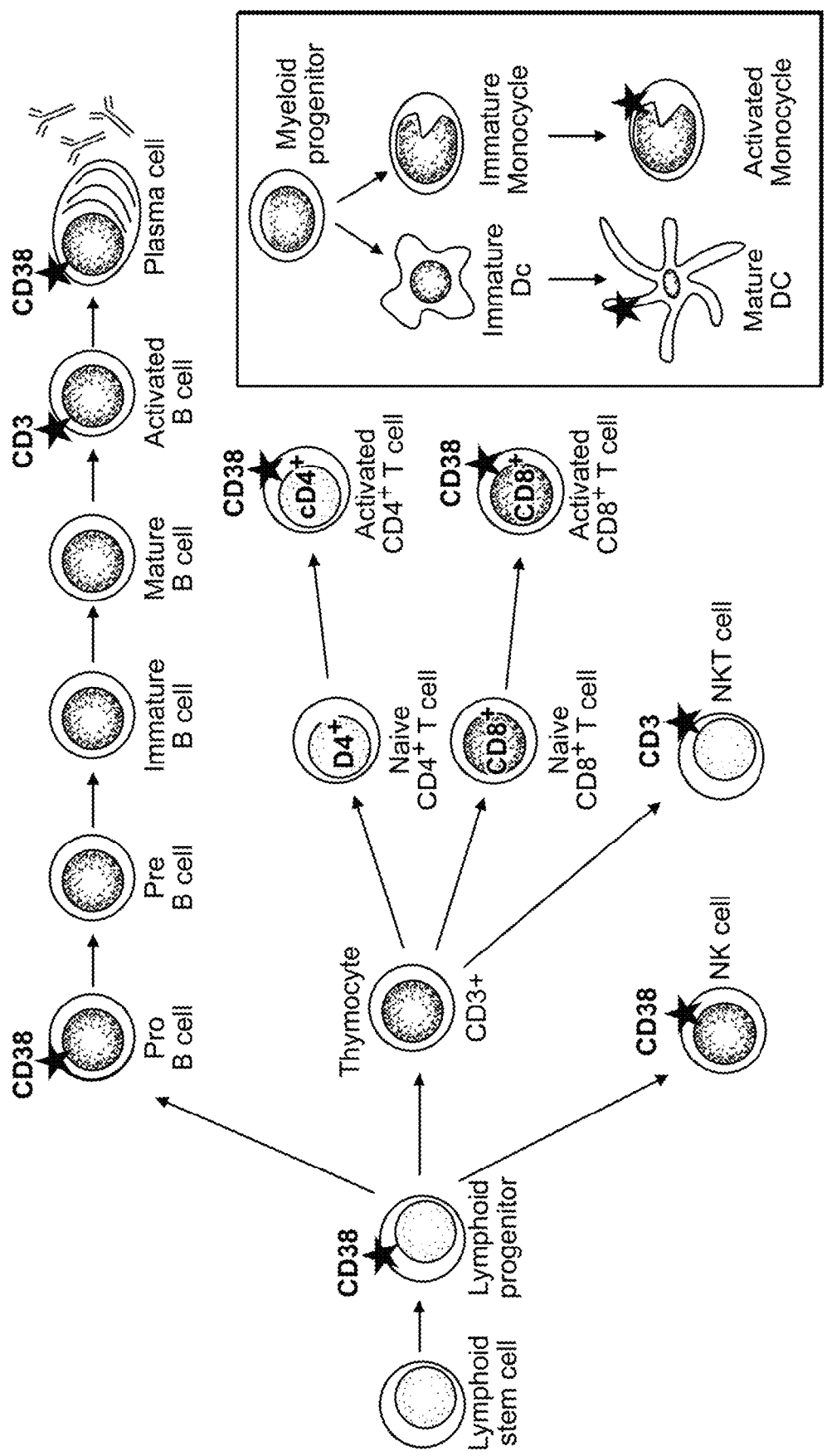
FIG. 1 depicts the CD38 Expression Profile on Lymphoid Lineage Cells, with a star indicating high CD38 expression. CD38 expression has been identified on pro-B cells (CD34+CD19+CD20−), activated B cells (CD19+CD20+), plasma cells (CD138+CD19−CD20−), activated CD4+ and CD8+ T cells, NKT cells (CD3+CD56+) and NK cells (CD56+CD16+). In addition, CD38 expression is found on lymphoid progenitor cells (CD34+CD45RA+CD10+CD19−) but not the lymphoid stem cell. In addition, increased CD38 expression is seen on mature DCs and activated monocytes.
Figure 2A:
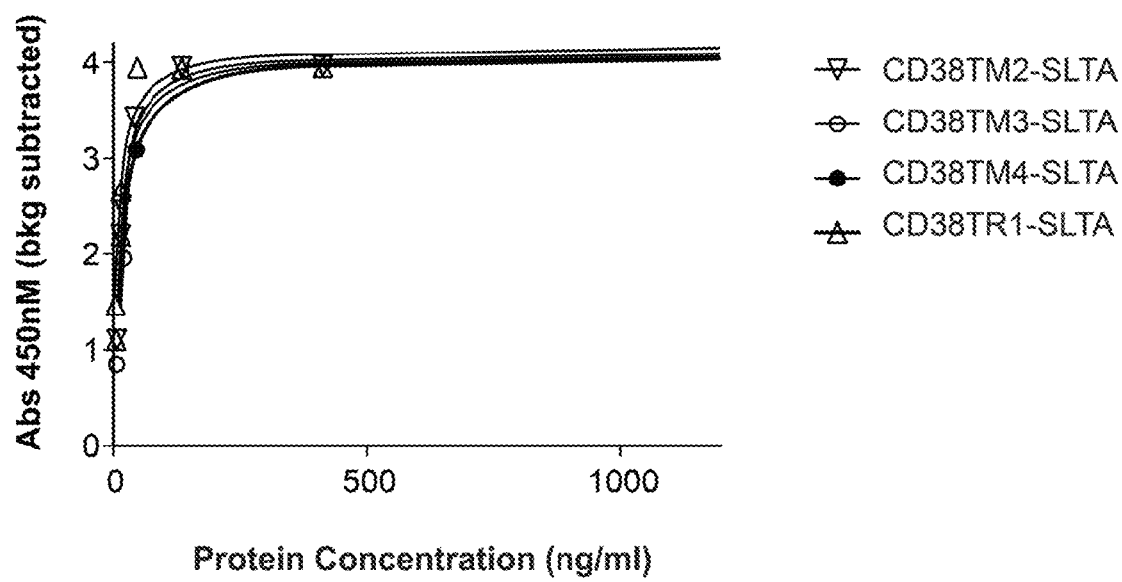
FIGS. 2A-2B show binding of anti-CD38 binding clones to purified human CD38 by ELISA assay. Each anti-CD38 binding clone was formatted into an scFv and then fused to a Shiga toxin A subunit (scFv-SLTA fusion format).
Figure 2B:
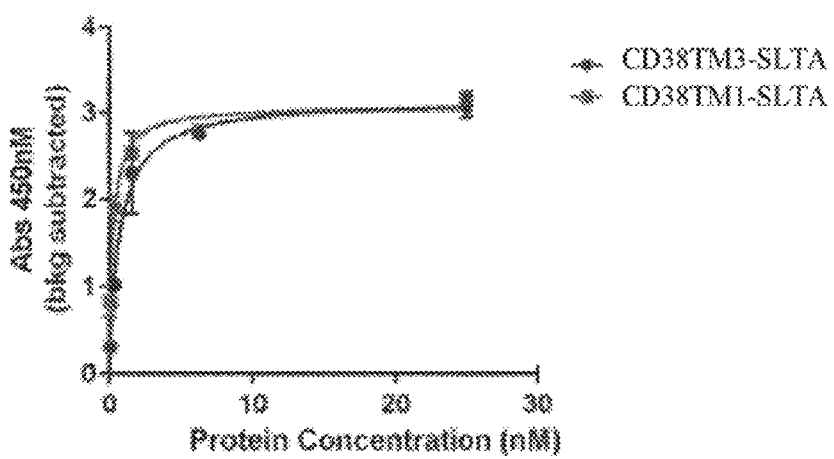
Figure 3A:
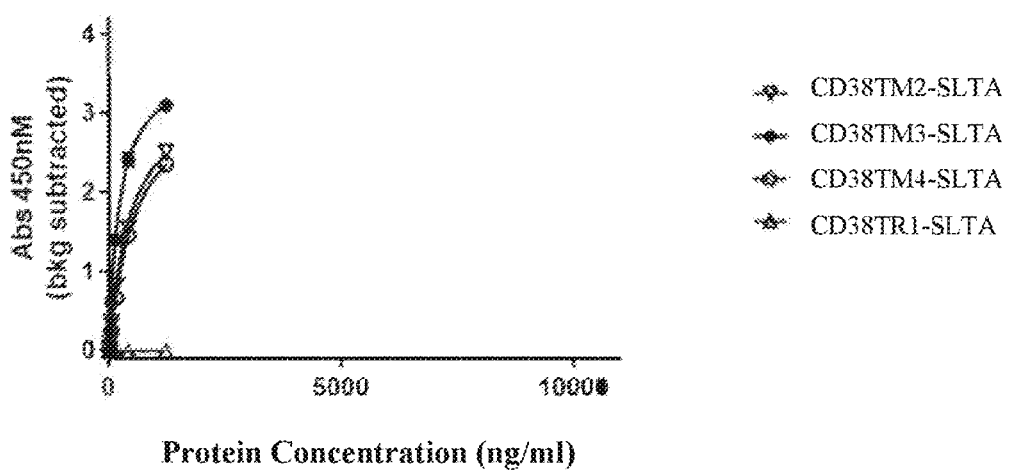
FIGS. 3A-3B show binding of anti-CD38 binding clones to purified cynomolgus CD38 by ELISA assay. Each anti-CD38 binding clone was formatted into an scFv and then fused to a Shiga toxin A Subunit.
Figure 3B:
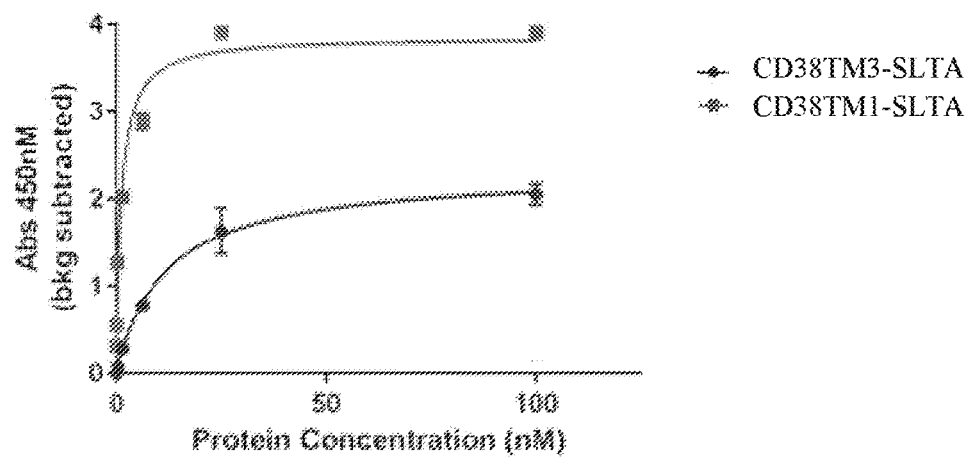
Figure 4:
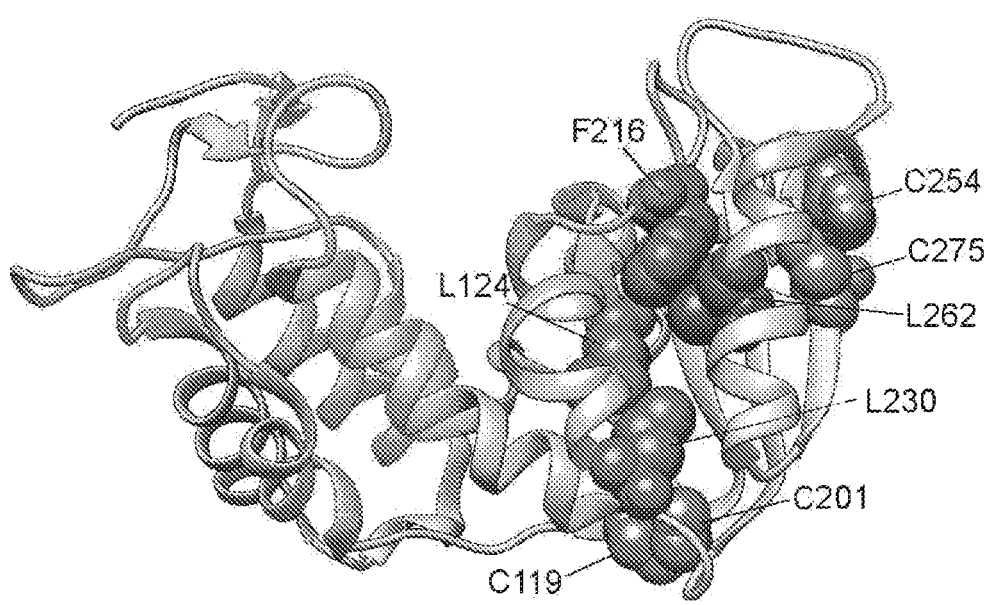
Figure 5A:
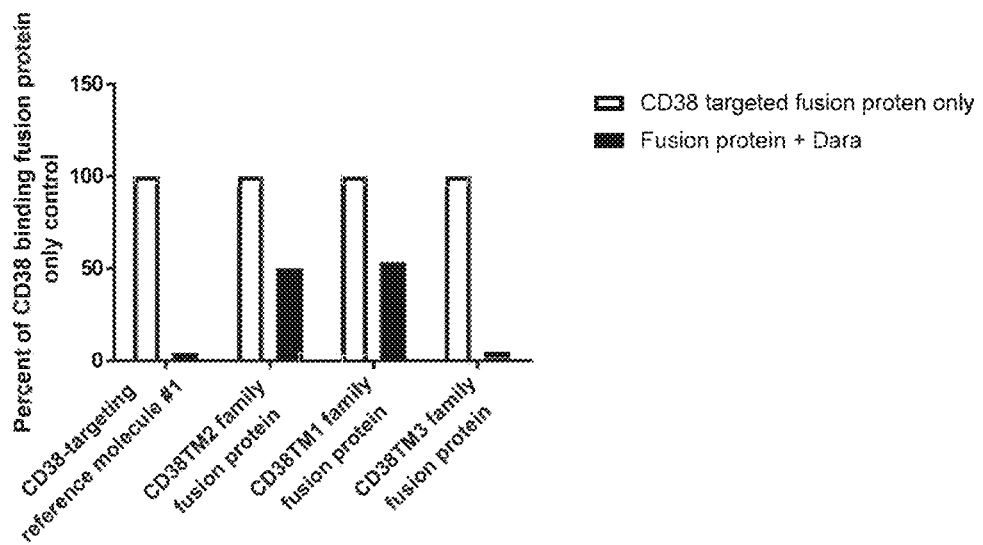
Figure 5B:
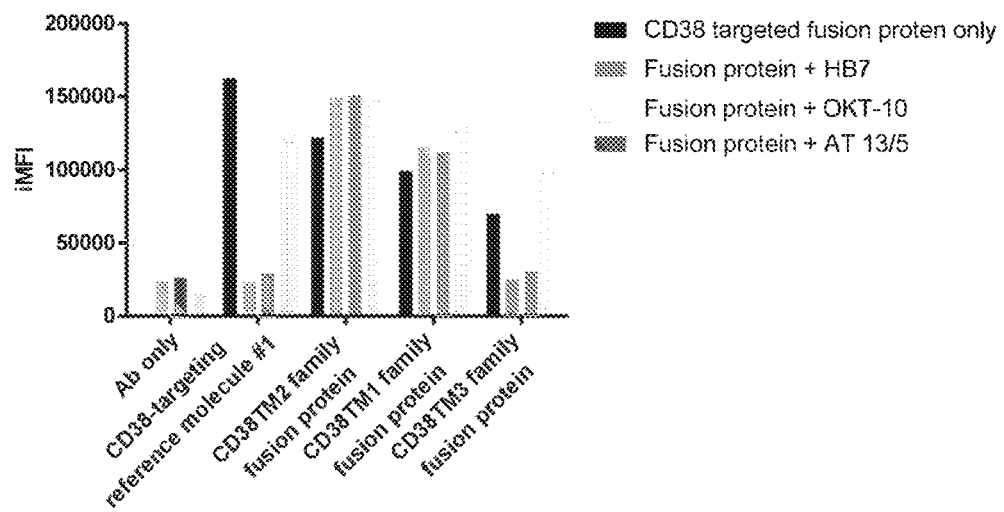

As shown in FIGS. 5A and 5B, CD38TM1 and CD38TM2 in the scFv SLTA fusion protein format are able to bind to CD38 in the presence of daratumumab, HB-7, AT13-5, and OKT-10, indicating that they bind to an epitope on CD38 different from the epitope(s) bound by daratumumab, HB-7, AT13-5, and OKT-10. CD38TM3 in the scFv SLTA fusion protein format is able to bind to CD38 in the presence of OKT-10, but not daratumumab, HB-7 and AT13-5, indicating that CD38TM3 binds to an epitope on CD38 different from the epitope bound by OKT-10, and CD38TM3 shares or partially shares an epitope on CD38 with daratumumab, HB-7 and AT13-5.

Competitive binding among anti-CD38 antigen binding clones to CD38 was also tested. CD38TM2, CD38TM1 and CD38TM3 were formatted into scFv and fused to Shiga toxin A subunit as described above. MOLP-8 cells were incubated with 20 μg/ml of an anti-CD38 binding clone (~400 nM) or the control molecule (Shiga toxin A subunit alone) for 70 minutes. Then 0.5 μg/ml of an anti-CD38 antigen binding clone in the scFv SLTA fusion protein format was added and incubated with the cells for 48 hours. CD38 binding was detected by a primary antibody recognizing Shiga toxin A subunit, and a FITC conjugated anti-IgG secondary antibody followed by flow cytometry. Mean fluorescence intensity (MFI) of anti-CD38 antigen binding clones was calculated after subtracting the signal from the secondary antibody only control, and plotted as a percentage of MFI measured from Shiga toxin A subunit alone as a control. As shown in FIGS. 5C and 5D, CD38TM1 and CD38TM2 bind to CD38 in a competitive manner, consistent with the fact that they bind to the same epitope on CD38. CD38TM3 binds to CD38 in a semi-competitively manner with CD38TM1 and CD38TM2.

D. Induction of CDC and ADCC by Anti-CD38 Antibody

Anti-CD38 binding clones were formatted as human IgG1 and tested for their ability to induce complement-dependent cytotoxicity (CDC) and antibody-dependent cell-mediated cytotoxicity (ADCC).

For CDC assay, MOLP-8 cells were plated at a density of 10,000 cells per well in a black 96-well flat-bottom tissue culture plate in 50 μL of complete media (RPMI supplemented with 10% fetal bovine serum). 50 μL of anti-CD38 antibody (9 μg/ml), control IgG1 antibody (9 μg/ml), or media alone was added to each well and left to incubate at room temperature (RT) for 10 min. Varying amounts (2-15 μL) of purified rabbit complement (Cat #CL 3441 Cedarlane Laboratories, Canada) was added to each well except control wells. After one-hour incubation at 37° C., the plate was brought to room temperature, 100 μL of cell titer CytoTox Glo™ reagent (Promega G7571/G7573) was added to each well, the plate was shaken for 5 to 7 minutes, and luminescence was read on an EnVision® (Perkin Elmer) luminescence plate reader. The conditions tested were: cells alone; cells+complement; cells+IgG1 control+complement; cells+ antibody+complement. % CDC was calculated using the following equation: 100−(RLUT/RLUC)×100), where RLUT is the relative luminescence units of the test sample and RLUc is the relative luminescence units of the sample with complement alone. The assay was conducted in triplicates, and statistical analysis was performed using PRISM software.

For measuring ADCC, MOLP-8 cells were used as target cells. Peripheral blood mononuclear cells (PBMCs) were isolated as effector cells by Ficoll-Plaque™ separation from buffy coat or LRS which were obtained from the Stanford Blood Center (Palo Alto, Calif.). Specimens were diluted 1:3 with 2% FBS in PBS. 15 mL of Ficoll-Plaque™ (GE Healthcare) was gently layered under 35 mL of diluted specimen and centrifuged at 1800 rpm (brake off) for 25 minutes. The cloudy interphase containing PBMCs was collected, washed 3 times in 2% FBS/PBS and frozen into aliquots of 50×10⁶ cells/mL per aliquot in 10% DMSO/FBS. Before use, frozen aliquots of PBMCs were thawed and cultured overnight in 10% FBS/RPMI+5 ng/mL recombinant human I12 (R & D systems #202-IL) at 2×10⁶ cells per mL.

For the ADCC assay, all steps were performed in complete media. 5000 target cells were plated per well in a 96-well plate, and 50 μL of anti-CD38 antibody (10 μg/ml), control IgG1 (10 μg/ml), or media alone was added to each well. 50 μL of human effector PBMCs was then added to the wells at a ratio of between 1:25 to 1:50 for target:effector (T:E) cells. The plate was briefly centrifuged for 30 seconds at 800 rpm to bring all cells into close proximity. After 4 hours of incubation at 37° C., the plate was centrifuged at 1100 rpm for 5 minutes and 100 μL supernatant was transferred to a white plate. 100 μL CytoTox Glo™ reagent (Promega cat #G9292) was added to the supernatant and the plate was then shaked for 20-30 minutes at RT. Luminescence was read on an EnVision® (Perkin Elmer) luminescence plate reader and percentage of specific lysis was calculated using the following equation: (RLUT/RLUE/T)/ (RLUL/RLUE/T)×100, where RLUT is the relative luminescence units of the test sample and RLUE/T is the relative luminescence units of the sample containing target cells and effector cells alone, and RLUL is the relative luminescence units for cells lysed with Triton X-100. The assay was conducted in triplicates, and statistical analysis was performed using PRISM software.

The percentages of CDC and ADCC induced by anti-CD38 antibody clones are shown in Table 6. All anti-CD38 antibody clones are capable of inducing CDC and ADCC towards CD38 expressing cells.

TABLE 6

| Clones | % CDC (mean) | % ADCC (mean) |
| --- | --- | --- |
| CD38TM3 | 16.3 | 49.2 |
| CD38TM1 | 15.0 | 29.0 |
| CD38TM2 | 7.2 | 31.8 |
| CD38TM5 | 4.7 | 35.2 |
| CD38TM6 | 34.3 | 50.4 |

E. Derivation of CD38TM4 from CD38TM3

Figure 11B:
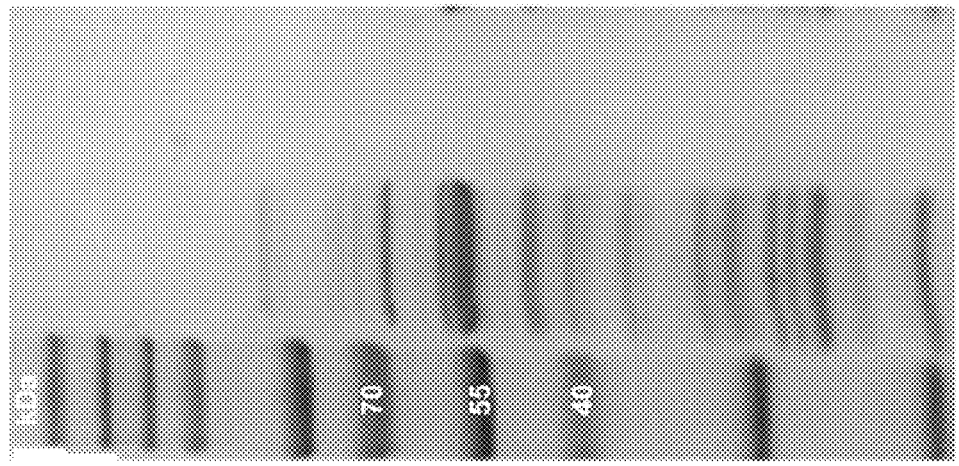
Figure 11A:
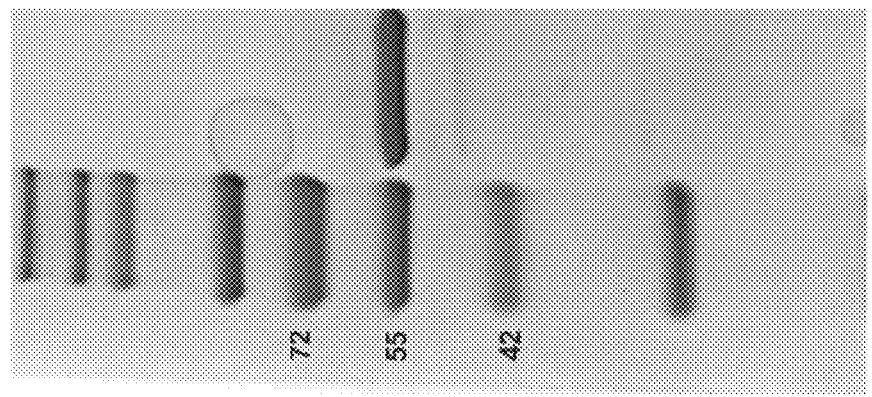

VH and VL of CD38TM3 do not bind to standard monoclonal antibody purification resins (protein A or protein L), and it was purified using the His-tag and IMAC column (FIG. 11A showing purification of CD38TM3 in the scFv-SLTA fusion protein format as an example). In order to render easier purification, the light chain of CD38TM3 which is a Lambda light chain was modified by framework mutations so that it is able to bind to Protein L, allowing for affinity purification without an additional tag. As show in FIG. 11C, the first 21 amino acids of CD38TM3 VL domain was replaced with the first 22 amino acids of the VL domain of CD38TR1, which is a Kappa light chain to derive the VL domain of CD38TM4. The resulting CD38TM4 is able to bind to protein L and thus was purified by Protein L column (FIG. 11B showing purification of CD38TM4 in the scFv-SLTA fusion protein format as an example).

```
                       SEQUENCE LISTING

Sequence total quantity: 68
SEQ ID NO: 1            moltype = AA   length = 123
FEATURE                 Location/Qualifiers
REGION                  1..123
                        note = CD38-Targeting Moiety
source                  1..123
                        mol_type = protein
                        organism = synthetic construct
SEQUENCE: 1
QVQLVQSGAE VKKPGESLKI SCKGSGYSFT SYWIGWVRQM PGKGLEWMGI IYPGDSDTRY   60
SPSFQGQVTI SADKSISTAY LQWSSLKASD TAMYYCARGP STGFWSGNYF DYWGQGTLVT  120
VSS                                                                123

SEQ ID NO: 2            moltype = AA   length = 8
FEATURE                 Location/Qualifiers
REGION                  1..8
                        note = CD38-Targeting Moiety
source                  1..8
                        mol_type = protein
                        organism = synthetic construct
SEQUENCE: 2
GYSFTSYW                                                             8

SEQ ID NO: 3            moltype = AA   length = 8
FEATURE                 Location/Qualifiers
REGION                  1..8
                        note = CD38-Targeting Moiety
source                  1..8
                        mol_type = protein
                        organism = synthetic construct
SEQUENCE: 3
IYPGDSDT                                                             8

SEQ ID NO: 4            moltype = AA   length = 16
FEATURE                 Location/Qualifiers
REGION                  1..16
                        note = CD38-Targeting Moiety
source                  1..16
                        mol_type = protein
                        organism = synthetic construct
SEQUENCE: 4
ARGPSTGFWS GNYFDY                                                   16

SEQ ID NO: 5            moltype = AA   length = 110
FEATURE                 Location/Qualifiers
REGION                  1..110
                        note = CD38-Targeting Moiety
source                  1..110
                        mol_type = protein
                        organism = synthetic construct
SEQUENCE: 5
QTVVTQEPSL TVSPGETVTL TCASSTGAVT SGFYPNWFQQ KPGQAPRALI YATNNKYSWT   60
PARFSGSLLG DKAALTLSRV QPEDEADYYC LVYYDGAWVF GGGTKLTVLG             110

SEQ ID NO: 6            moltype = AA   length = 9
FEATURE                 Location/Qualifiers
REGION                  1..9
                        note = CD38-Targeting Moiety
source                  1..9
                        mol_type = protein
                        organism = synthetic construct
SEQUENCE: 6
TGAVTSGFY                                                            9

SEQ ID NO: 7            moltype =    length =
SEQUENCE: 7
000

SEQ ID NO: 8            moltype = AA   length = 8
FEATURE                 Location/Qualifiers
REGION                  1..8
```

```
                            note = CD38-Targeting Moiety
source                      1..8
                            mol_type = protein
                            organism = synthetic construct
SEQUENCE: 8
LVYYDGAW                                                                   8

SEQ ID NO: 9                moltype = AA   length = 120
FEATURE                     Location/Qualifiers
REGION                      1..120
                            note = CD38-Targeting Moiety
source                      1..120
                            mol_type = protein
                            organism = synthetic construct
SEQUENCE: 9
EVQLLESGGG LVQPGGSLRL SCAASGFTFS DYYMSWVRQA PGKGLEWVSA ISGSGGSTYY            60
ADSVKGRFTI SRDNSKNTLY LQMNSLRAED TAVYYCAREH SNYFYGMDVW GQGTLVTVSS           120

SEQ ID NO: 10               moltype = AA   length = 8
FEATURE                     Location/Qualifiers
REGION                      1..8
                            note = CD38-Targeting Moiety
source                      1..8
                            mol_type = protein
                            organism = synthetic construct
SEQUENCE: 10
GFTFSDYY                                                                   8

SEQ ID NO: 11               moltype = AA   length = 8
FEATURE                     Location/Qualifiers
REGION                      1..8
                            note = CD38-Targeting Moiety
source                      1..8
                            mol_type = protein
                            organism = synthetic construct
SEQUENCE: 11
ISGSGGST                                                                   8

SEQ ID NO: 12               moltype = AA   length = 13
FEATURE                     Location/Qualifiers
REGION                      1..13
                            note = CD38-Targeting Moiety
source                      1..13
                            mol_type = protein
                            organism = synthetic construct
SEQUENCE: 12
AREHSNYFYG MDV                                                            13

SEQ ID NO: 13               moltype = AA   length = 112
FEATURE                     Location/Qualifiers
REGION                      1..112
                            note = CD38-Targeting Moiety
source                      1..112
                            mol_type = protein
                            organism = synthetic construct
SEQUENCE: 13
QSVLTQPPSA SGTPGQRVTI SCSGSSSNIG SNYVYWYQQL PGTAPKLLIY GNSNRPSGVP           60
DRFSGSKSGT SASLAISGLR SEDEADYYCQ SYDSSLSGSG VFGGGTKLTV LG                  112

SEQ ID NO: 14               moltype = AA   length = 8
FEATURE                     Location/Qualifiers
REGION                      1..8
                            note = CD38-Targeting Moiety
source                      1..8
                            mol_type = protein
                            organism = synthetic construct
SEQUENCE: 14
SSNIGSNY                                                                   8

SEQ ID NO: 15               moltype =      length =
SEQUENCE: 15
000

SEQ ID NO: 16               moltype = AA   length = 11
FEATURE                     Location/Qualifiers
REGION                      1..11
                            note = CD38-Targeting Moiety
source                      1..11
                            mol_type = protein
```

```
                                organism = synthetic construct
SEQUENCE: 16
QSYDSSLSGS G                                                                   11

SEQ ID NO: 17           moltype = AA   length = 119
FEATURE                 Location/Qualifiers
REGION                  1..119
                        note = CD38-Targeting Moiety
source                  1..119
                        mol_type = protein
                        organism = synthetic construct
SEQUENCE: 17
EVQLLESGGG LVQPGGSLRL SCAASGFTFS SYWMHWVRQA PGKGLEWVSA ISGSGGGTFY    60
ADSVKGRFTI SRDNSKNTLY LQMNSLRAED TAVYYCAREG ETSFGLDVWG QGTLVTVSS    119

SEQ ID NO: 18           moltype = AA   length = 8
FEATURE                 Location/Qualifiers
REGION                  1..8
                        note = CD38-Targeting Moiety
source                  1..8
                        mol_type = protein
                        organism = synthetic construct
SEQUENCE: 18
GFTFSSYW                                                                        8

SEQ ID NO: 19           moltype = AA   length = 8
FEATURE                 Location/Qualifiers
REGION                  1..8
                        note = CD38-Targeting Moiety
source                  1..8
                        mol_type = protein
                        organism = synthetic construct
SEQUENCE: 19
ISGSGGGT                                                                        8

SEQ ID NO: 20           moltype = AA   length = 12
FEATURE                 Location/Qualifiers
REGION                  1..12
                        note = CD38-Targeting Moiety
source                  1..12
                        mol_type = protein
                        organism = synthetic construct
SEQUENCE: 20
AREGETSFGL DV                                                                  12

SEQ ID NO: 21           moltype = AA   length = 111
FEATURE                 Location/Qualifiers
REGION                  1..111
                        note = CD38-Targeting Moiety
source                  1..111
                        mol_type = protein
                        organism = synthetic construct
SEQUENCE: 21
QSVLTQPPSA SGTPGQRVTI SCSGSSSNIG GNYVYWYQQL PGTAPKLLIY RNNQRPSGVP    60
DRFSGSKSGT SASLAISGLR SEDEADYYCQ SYDSSLSVSV FGGGTKLTVL G            111

SEQ ID NO: 22           moltype = AA   length = 8
FEATURE                 Location/Qualifiers
REGION                  1..8
                        note = CD38-Targeting Moiety
source                  1..8
                        mol_type = protein
                        organism = synthetic construct
SEQUENCE: 22
SSNIGGNY                                                                        8

SEQ ID NO: 23           moltype =      length =
SEQUENCE: 23
000

SEQ ID NO: 24           moltype = AA   length = 10
FEATURE                 Location/Qualifiers
REGION                  1..10
                        note = CD38-Targeting Moiety
source                  1..10
                        mol_type = protein
                        organism = synthetic construct
SEQUENCE: 24
QSYDSSLSVS                                                                     10
```

```
SEQ ID NO: 25            moltype = AA  length = 111
FEATURE                  Location/Qualifiers
REGION                   1..111
                         note = CD38-Targeting Moiety
source                   1..111
                         mol_type = protein
                         organism = synthetic construct
SEQUENCE: 25
DIQMTQSPSS LSASVGDRVT ITCASSTGAV TSGFYPNWFQ QKPGQAPRAL IYATNNKYSW    60
TPARFSGSLL GDKAALTLSR VQPEDEADYY CLVYYDGAWV FGGGTKLTVL G            111

SEQ ID NO: 26            moltype = AA  length = 119
FEATURE                  Location/Qualifiers
REGION                   1..119
                         note = CD38-Targeting reference molecule
source                   1..119
                         mol_type = protein
                         organism = synthetic construct
SEQUENCE: 26
QVQLQESGPG LVRPSQTLSL TCTVSGFSLT SYGVHWVRQP PGRGLEWIGV MWRGGSTDYN    60
AAFMSRLNIT KDNSKNQVSL RLSSVTAADT AVYYCAKSMI TTGFVMDSWG QGSLVTVSS    119

SEQ ID NO: 27            moltype = AA  length = 107
FEATURE                  Location/Qualifiers
REGION                   1..107
                         note = CD38-Targeting reference molecule
source                   1..107
                         mol_type = protein
                         organism = synthetic construct
SEQUENCE: 27
DIQMTQSPSS LSASVGDRVT ITCKASEDIY NRLTWYQQKP GKAPKLLISG ATSLETGVPS    60
RFSGSGSGTD FTFTISSLQP EDIATYYCQQ YWSNPYTFGQ GTKVEIK                 107

SEQ ID NO: 28            moltype = AA  length = 300
FEATURE                  Location/Qualifiers
REGION                   1..300
                         note = CD38 Homo sapiens
source                   1..300
                         mol_type = protein
                         organism = synthetic construct
SEQUENCE: 28
MANCEFSPVS GDKPCCRLSR RAQLCLGVSI LVLILVVVLA VVVPRWRQQW SGPGTTKRFP    60
ETVLARCVKY TEIHPEMRHV DCQSVWDAFK GAFISKHPCN ITEEDYQPLM KLGTQTVPCN   120
KILLWSRIKD LAHQFTQVQR DMFTLEDTLL GYLADDLTWC GEFNTSKINY QSCPDWRKDC   180
SNNPVSVFWK TVSRRFAEAA CDVVHVMLNG SRSKIFDKNS TFGSVEVHNL QPEKVQTLEA   240
WVIHGGREDS RDLCQDPTIK ELESIISKRN IQFSCKNIYR PDKFLQCVKN PEDSSCTSEI   300

SEQ ID NO: 29            moltype = AA  length = 258
FEATURE                  Location/Qualifiers
REGION                   1..258
                         note = CD38 Homo sapiens extracellular domain
source                   1..258
                         mol_type = protein
                         organism = synthetic construct
SEQUENCE: 29
VPRWRQQWSG PGTTKRFPET VLARCVKYTE IHPEMRHVDC QSVWDAFKGA FISKHPCNIT    60
EEDYQPLMKL GTQTVPCNKI LLWSRIKDLA HQFTQVQRDM FTLEDTLLGY LADDLTWCGE   120
FNTSKINYQS CPDWRKDCSN NPVSVFWKTV SRRFAEAACD VVHVMLNGSR SKIFDKNSTF   180
GSVEVHNLQP EKVQTLEAWV IHGGREDSRD LCQDPTIKEL ESIISKRNIQ FSCKNIYRPD   240
KFLQCVKNPE DSSCTSEI                                                 258

SEQ ID NO: 30            moltype = AA  length = 301
FEATURE                  Location/Qualifiers
REGION                   1..301
                         note = CD38 Macaca fascicularis
source                   1..301
                         mol_type = protein
                         organism = synthetic construct
SEQUENCE: 30
MANCEFSPVS GDKPCCRLSR RAQVCLGVCL LVLLILVVVV AVVLPRWRQQ WSGSGTTSRF    60
PETVLARCVK YTEVHPEMRH VDCQSVWDAF KGAFISKYPC NITEEDYQPL VKLGTQTVPC   120
NKTLLWSRIK DLAHQFTQVQ RDMFTLEDML LGYLADDLTW CGEFNTFEIN YQSCPDWRKD   180
CSNNPVSVFW KTVSRRFAET ACGVVHVMLN GSRSKIFDKN STFGSVEVHN LQPEKVQALE   240
AWVIHGGRED SRDLCQDPTI KELESIISKR NIRFFCKNIY RPDKFLQCVK NPEDSSCLSG   300
I                                                                   301

SEQ ID NO: 31            moltype = AA  length = 258
FEATURE                  Location/Qualifiers
```

| | | |
|---|---|---|
| REGION | 1..258<br>note = CD38 Macaca fascicularis extracellular domain | |
| source | 1..258<br>mol_type = protein<br>organism = synthetic construct | |
| SEQUENCE: 31 | | |
| LPRWRQQWSG SGTTSRFPET VLARCVKYTE VHPEMRHVDC QSVWDAFKGA FISKYPCNIT | | 60 |
| EEDYQPLVKL GTQTVPCNKT LLWSRIKDLA HQFTQVQRDM FTLEDMLLGY LADDLTWCGE | | 120 |
| FNTFEINYQS CPDWRKDCSN NPVSVFWKTV SRRFAETACG VVHVMLNGSR SKIFDKNSTF | | 180 |
| GSVEVHNLQP EKVQALEAWV IHGGREDSRD LCQDPTIKEL ESIISKRNIR FFCKNIYRPD | | 240 |
| KFLQCVKNPE DSSCLSGI | | 258 |
| | | |
| SEQ ID NO: 32 | moltype = AA length = 15 | |
| FEATURE | Location/Qualifiers | |
| REGION | 1..15<br>note = Linker sequence | |
| source | 1..15<br>mol_type = protein<br>organism = synthetic construct | |
| SEQUENCE: 32 | | |
| GGGGSGGGGS GGGGS | | 15 |
| | | |
| SEQ ID NO: 33 | moltype = length = | |
| SEQUENCE: 33 | | |
| 000 | | |
| | | |
| SEQ ID NO: 34 | moltype = AA length = 4 | |
| FEATURE | Location/Qualifiers | |
| REGION | 1..4<br>note = Linker sequence | |
| source | 1..4<br>mol_type = protein<br>organism = synthetic construct | |
| SEQUENCE: 34 | | |
| GGGS | | 4 |
| | | |
| SEQ ID NO: 35 | moltype = AA length = 5 | |
| FEATURE | Location/Qualifiers | |
| REGION | 1..5<br>note = Linker sequence | |
| source | 1..5<br>mol_type = protein<br>organism = synthetic construct | |
| SEQUENCE: 35 | | |
| GGGGS | | 5 |
| | | |
| SEQ ID NO: 36 | moltype = AA length = 8 | |
| FEATURE | Location/Qualifiers | |
| REGION | 1..8<br>note = Linker sequence | |
| source | 1..8<br>mol_type = protein<br>organism = synthetic construct | |
| SEQUENCE: 36 | | |
| GGGGSGGG | | 8 |
| | | |
| SEQ ID NO: 37 | moltype = AA length = 7 | |
| FEATURE | Location/Qualifiers | |
| REGION | 1..7<br>note = Linker sequence | |
| source | 1..7<br>mol_type = protein<br>organism = synthetic construct | |
| SEQUENCE: 37 | | |
| GGSGGGG | | 7 |
| | | |
| SEQ ID NO: 38 | moltype = AA length = 18 | |
| FEATURE | Location/Qualifiers | |
| REGION | 1..18<br>note = Linker sequence | |
| source | 1..18<br>mol_type = protein<br>organism = synthetic construct | |
| SEQUENCE: 38 | | |
| GSTSGGGSGG GSGGGGSS | | 18 |
| | | |
| SEQ ID NO: 39 | moltype = AA length = 330 | |
| FEATURE | Location/Qualifiers | |
| REGION | 1..330 | |

-continued

```
                         note     = Human IgG1 constant region
source                   1..330
                         mol_type = protein
                         organism = synthetic construct
SEQUENCE: 39
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 40            moltype = AA  length = 526
FEATURE                  Location/Qualifiers
REGION                   1..526
                         note    = CD38 targeting moiety-SLTA
source                   1..526
                         mol_type = protein
                         organism = synthetic construct
SEQUENCE: 40
MKEFTLDFST AKTYVDSLNV IRSAIGTPLQ TISSGGTSLL MIDSGIGDNL FAVDILGFDF    60
TLGRFNNLRL IVERNNLYVT GFVNRTNNVF YRFADFSHVT FPGTTAVTLS ADSSYTTLQR   120
VAGISRTGMQ INRHSLTTSY LDLMSHSGTS LTQSVARAML RFVTVTAEAL RFRQIQRGFR   180
TTLDDLSGAS YVMTAEDVDL TLNWGRLSSV LPDYHGQDSV RVGRISFGSI NAILGSVALI   240
LNSHHHASAV AAEFPKPSTP PGSSGGAPQS VLTQPPSASG TPGQRVTISC SGSSSNIGSN   300
YVYWYQQLPG TAPKLLIYGN SNRPSGVPDR FSGSKSGTSA SLAISGLRSE DEADYYCQSY   360
DSSLSGSGVF GGGTKLTVLG GGGGSGGGGS GGGGSGGGGS GGGGSSEVQL LESGGGLVQP   420
GGSLRLSCAA SGFTFSDYYM SWVRQAPGKG LEWVSAISGS GGSTYYADSV KGRFTISRDN   480
SKNTLYLQMN SLRAEDTAVY YCAREHSNYF YGMDVWGQGT LVTVSS                 526

SEQ ID NO: 41            moltype = AA  length = 503
FEATURE                  Location/Qualifiers
REGION                   1..503
                         note    = CD38 targeting moiety-SLTA
source                   1..503
                         mol_type = protein
                         organism = synthetic construct
SEQUENCE: 41
MKEFTLDFST AKTYVDSLNV IRSAIGTPLQ TISSGGTSLL MIDSGIGDNL FAVDILGFDF    60
TLGRFNNLRL IVERNNLYVT GFVNRTNNVF YRFADFSHVT FPGTTAVTLS ADSSYTTLQR   120
VAGISRTGMQ INRHSLTTSY LDLMSHSGTS LTQSVARAML RFVTVTAEAL RFRQIQRGFR   180
TTLDDLSGAS YVMTAEDVDL TLNWGRLSSV LPDYHGQDSV RVGRISFGSI NAILGSVALI   240
LNSHHHASAV AAEFPKPSTP PGSSGGAPQS VLTQPPSASG TPGQRVTISC SGSSSNIGGN   300
YVYWYQQLPG TAPKLLIYRN NQRPSGVPDR FSGSKSGTSA SLAISGLRSE DEADYYCQSY   360
DSSLSVSVFG GGTKLTVLGG GGGSEVQLLE SGGGLVQPGG SLRLSCAASG FTFSSYWMHW   420
VRQAPGKGLE WVSAISGSGG GTFYADSVKG RFTISRDNSK NTLYLQMNSL RAEDTAVYYC   480
AREGETSFGL DVWGQGTLVT VSS                                          503

SEQ ID NO: 42            moltype = AA  length = 506
FEATURE                  Location/Qualifiers
REGION                   1..506
                         note    = CD38 targeting moiety-SLTA
source                   1..506
                         mol_type = protein
                         organism = synthetic construct
SEQUENCE: 42
MKEFTLDFST AKTYVDSLNV IRSAIGTPLQ TISSGGTSLL MIDSGIGDNL FAVDILGFDF    60
TLGRFNNLRL IVERNNLYVT GFVNRTNNVF YRFADFSHVT FPGTTAVTLS ADSSYTTLQR   120
VAGISRTGMQ INRHSLTTSY LDLMSHSGTS LTQSVARAML RFVTVTAEAL RFRQIQRGFR   180
TTLDDLSGAS YVMTAEDVDL TLNWGRLSSV LPDYHGQDSV RVGRISFGSI NAILGSVALI   240
LNSHHHASAV AAEFPKPSTP PGSSGGAPQV QLVQSGAEVK KPGESLKISC KGSGYSFTSY   300
WIGWVRQMPG KGLEWMGIIY PGDSDTRYSP SFQGQVTISA DKSISTAYLQ WSSLKASDTA   360
MYYCARGPST GFWSGNYFDY WGQGTLVTVS SGGGGSQTVV TQEPSLTVSP GETVTLTCAS   420
STGAVTSGFY PNWFQQKPGQ APRALIYATN NKYSWTPARF SGSLLGDKAA LTLSRVQPED   480
EADYYCLVYY DGAWVFGGGT KLTVLG                                       506

SEQ ID NO: 43            moltype = AA  length = 507
FEATURE                  Location/Qualifiers
REGION                   1..507
                         note    = CD38 targeting moiety-SLTA
source                   1..507
                         mol_type = protein
                         organism = synthetic construct
SEQUENCE: 43
MKEFTLDFST AKTYVDSLNV IRSAIGTPLQ TISSGGTSLL MIDSGIGDNL FAVDILGFDF    60
TLGRFNNLRL IVERNNLYVT GFVNRTNNVF YRFADFSHVT FPGTTAVTLS ADSSYTTLQR   120
VAGISRTGMQ INRHSLTTSY LDLMSHSGTS LTQSVARAML RFVTVTAEAL RFRQIQRGFR   180
TTLDDLSGAS YVMTAEDVDL TLNWGRLSSV LPDYHGQDSV RVGRISFGSI NAILGSVALI   240
LNSHHHASAV AAEFPKPSTP PGSSGGAPQV QLVQSGAEVK KPGESLKISC KGSGYSFTSY   300
```

```
WIGWVRQMPG KGLEWMGIIY PGDSDTRYSP SFQGQVTISA DKSISTAYLQ WSSLKASDTA    360
MYYCARGPST GFWSGNYFDY WGQGTLVTVS SGGGGSDIQM TQSPSSLSAS VGDRVTITCA    420
SSTGAVTSGF YPNWFQQKPG QAPRALIYAT NNKYSWTPAR FSGSLLGDKA ALTLSRVQPE    480
DEADYYCLVY YDGAWVFGGG TKLTVLG                                        507

SEQ ID NO: 44           moltype = AA   length = 499
FEATURE                 Location/Qualifiers
REGION                  1..499
                        note = CD38 targeting moiety-SLTA
source                  1..499
                        mol_type = protein
                        organism = synthetic construct
SEQUENCE: 44
MKEFTLDFST AKTYVDSLNV IRSAIGTPLQ TISSGGTSLL MIDSGSGDNL FAVDVRGIDP    60
EEGRFNNLRL IVERNNLYVT GFVNRTNNVF YRFADFSHVT FPGTTAVTLS GDSSYTTLQR    120
VAGISRTGMQ INRHSLTTSY LDLMSHSGTS LTQSVARAML RFVTVTAEAL RFRQIQRGFR    180
TTLDDLSGRS YVMTAEDVDL TLNWGRLSSV LPDYHGQDSV RVGRISFGSI NAILGSVALI    240
LNCHHHASAV AAEFPKPSTP PGSSGGAPDI QMTQSPSSLS ASVGDRVTIT CKASEDIYNR    300
LTWYQQKPGK APKLLISGAT SLETGVPSRF SGSGSGTDFT FTISSLQPED IATYYCQQYW    360
SNPYTFGQGT KVEIKGGGGS QVQLQESGPG LVRPSQTLSL TCTVSGFSLT SYGVHWVRQP    420
PGRGLEWIGV MWRGGSTDYN AAFMSRLNIT KDNSKNQVSL RLSSVTAADT AVYYCAKSMI    480
TTGFVMDSWG QGSLVTVSS                                                 499

SEQ ID NO: 45           moltype = AA   length = 330
FEATURE                 Location/Qualifiers
REGION                  1..330
                        note = Human IgG1 D265A constant region
source                  1..330
                        mol_type = protein
                        organism = synthetic construct
SEQUENCE: 45
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVAVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                     330

SEQ ID NO: 46           moltype = AA   length = 330
FEATURE                 Location/Qualifiers
REGION                  1..330
                        note = Human IgG1 N297A constant region
source                  1..330
                        mol_type = protein
                        organism = synthetic construct
SEQUENCE: 46
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                     330

SEQ ID NO: 47           moltype = AA   length = 326
FEATURE                 Location/Qualifiers
REGION                  1..326
                        note = Human IgG2 constant region
source                  1..326
                        mol_type = protein
                        organism = synthetic construct
SEQUENCE: 47
ASTKGPSVFP LAPCSRSTSE STAALGCLVK DYFPEPVTVS WNSGALTSGV HTFPAVLQSS    60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDIAVEW ESNGQPENNY KTTPPMLDSD GSFFLYSKLT VDKSRWQQGN    300
VFSCSVMHEA LHNHYTQKSL SLSPGK                                         326

SEQ ID NO: 48           moltype = AA   length = 377
FEATURE                 Location/Qualifiers
REGION                  1..377
                        note = Human IgG3 constant region
source                  1..377
                        mol_type = protein
                        organism = synthetic construct
SEQUENCE: 48
ASTKGPSVFP LAPCSRSTSG GTAALGCLVK DYFPEPVTVS WNSGALTSGV HTFPAVLQSS    60
GLYSLSSVVT VPSSSLGTQT YTCNVNHKPS NTKVDKRVEL KTPLGDTTHT CPRCPEPKSC    120
DTPPPCPRCP EPKSCDTPPP CPRCPEPKSC DTPPPCPRCP APELLGGPSV FLFPPKPKDT    180
```

```
LMISRTPEVT CVVVDVSHED PEVQFKWYVD GVEVHNAKTK PREEQYNSTF RVVSVLTVLH    240
QDWLNGKEYK CKVSNKALPA PIEKTISKTK GQPREPQVYT LPPSREEMTK NQVSLTCLVK    300
GFYPSDIAVE WESSGQPENN YNTTPPMLDS DGSFFLYSKL TVDKSRWQQG NIFSCSVMHE    360
ALHNRFTQKS LSLSPGK                                                  377

SEQ ID NO: 49           moltype = AA  length = 327
FEATURE                 Location/Qualifiers
REGION                  1..327
                        note = Human IgG4 constant region (Wild Type)
source                  1..327
                        mol_type = protein
                        organism = synthetic construct
SEQUENCE: 49
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSPGK                                       327

SEQ ID NO: 50           moltype = AA  length = 327
FEATURE                 Location/Qualifiers
REGION                  1..327
                        note = Human IgG4 constant region (S241P hinge mutant)
source                  1..327
                        mol_type = protein
                        organism = synthetic construct
SEQUENCE: 50
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSPGK                                       327

SEQ ID NO: 51           moltype = AA  length = 107
FEATURE                 Location/Qualifiers
REGION                  1..107
                        note = Human kappa light chain
source                  1..107
                        mol_type = protein
                        organism = synthetic construct
SEQUENCE: 51
RTVAAPSVFI FPPSDEQLKS GTASVVCLLN NFYPREAKVQ WKVDNALQSG NSQESVTEQD     60
SKDSTYSLSS TLTLSKADYE KHKVYACEVT HQGLSSPVTK SFNRGEC                 107

SEQ ID NO: 52           moltype = AA  length = 106
FEATURE                 Location/Qualifiers
REGION                  1..106
                        note = Human lambda light chain
source                  1..106
                        mol_type = protein
                        organism = synthetic construct
SEQUENCE: 52
GQPKAAPSVT LFPPSSEELQ ANKATLVCLI SDFYPGAVTV AWKADSSPVK AGVETTTPSK     60
QSNNKYAASS YLSLTPEQWK SHRSYSCQVT HEGSTVEKTV APTECS                  106

SEQ ID NO: 53           moltype = AA  length = 120
FEATURE                 Location/Qualifiers
REGION                  1..120
                        note = CD38-Targeting Moiety
source                  1..120
                        mol_type = protein
                        organism = synthetic construct
SEQUENCE: 53
EVQLLESGGG LVQPGGSLRL SCAASGFTFS DYYMNWIRQA PGKGLEWVSS ISSSSSYIYY     60
ADSVKGRFTI SRDNSKNTLY LQMNSLRAED TAVYYCATEG PYYLYGFDIW GQGTLVTVSS    120

SEQ ID NO: 54           moltype = AA  length = 8
FEATURE                 Location/Qualifiers
REGION                  1..8
                        note = CD38-Targeting Moiety
source                  1..8
                        mol_type = protein
                        organism = synthetic construct
SEQUENCE: 54
GFTFSDYY                                                              8

SEQ ID NO: 55           moltype = AA  length = 8
```

```
FEATURE                 Location/Qualifiers
REGION                  1..8
                        note = CD38-Targeting Moiety
source                  1..8
                        mol_type = protein
                        organism = synthetic construct
SEQUENCE: 55
ISSSSSYI                                                                 8

SEQ ID NO: 56           moltype = AA  length = 13
FEATURE                 Location/Qualifiers
REGION                  1..13
                        note = CD38-Targeting Moiety
source                  1..13
                        mol_type = protein
                        organism = synthetic construct
SEQUENCE: 56
ATEGPYYLYG FDI                                                           13

SEQ ID NO: 57           moltype = AA  length = 111
FEATURE                 Location/Qualifiers
REGION                  1..111
                        note = CD38-Targeting Moiety
source                  1..111
                        mol_type = protein
                        organism = synthetic construct
SEQUENCE: 57
QSVLTQPPSA SGTPGQRVTI SCSGSSSNIG SNYVYWYQQL PGTAPKLLIY GNSNRPSGVP         60
DRFSGSKSGT SASLAISGLR SEDEADYYCQ SYDNTLSGVI FGGGTKLTVL G                  111

SEQ ID NO: 58           moltype = AA  length = 8
FEATURE                 Location/Qualifiers
REGION                  1..8
                        note = CD38-Targeting Moiety
source                  1..8
                        mol_type = protein
                        organism = synthetic construct
SEQUENCE: 58
SSNIGSNY                                                                 8

SEQ ID NO: 59           moltype =     length =
SEQUENCE: 59
000

SEQ ID NO: 60           moltype = AA  length = 10
FEATURE                 Location/Qualifiers
REGION                  1..10
                        note = CD38-Targeting Moiety
source                  1..10
                        mol_type = protein
                        organism = synthetic construct
SEQUENCE: 60
QSYDNTLSGV                                                               10

SEQ ID NO: 61           moltype = AA  length = 123
FEATURE                 Location/Qualifiers
REGION                  1..123
                        note = CD38-Targeting Moiety
source                  1..123
                        mol_type = protein
                        organism = synthetic construct
SEQUENCE: 61
EVQLLESGGG LVQPGGSLRL SCAASGFTFD DYGMTWVRQA PGKGLEWVSG INWNGGSTGY         60
ADSVKGRFTI SRDNSKNTLY LQMNSLRAED TAVYYCARGG LFHDSSGYYF GHWGQGTLVT         120
VSS                                                                      123

SEQ ID NO: 62           moltype = AA  length = 8
FEATURE                 Location/Qualifiers
REGION                  1..8
                        note = CD38-Targeting Moiety
source                  1..8
                        mol_type = protein
                        organism = synthetic construct
SEQUENCE: 62
GFTFDDYG                                                                 8

SEQ ID NO: 63           moltype = AA  length = 8
FEATURE                 Location/Qualifiers
REGION                  1..8
```

```
                       note = CD38-Targeting Moiety
source                 1..8
                       mol_type = protein
                       organism = synthetic construct
SEQUENCE: 63
INWNGGST                                                              8

SEQ ID NO: 64          moltype = AA  length = 16
FEATURE                Location/Qualifiers
REGION                 1..16
                       note = CD38-Targeting Moiety
source                 1..16
                       mol_type = protein
                       organism = synthetic construct
SEQUENCE: 64
ARGGLFHDSS GYYFGH                                                    16

SEQ ID NO: 65          moltype = AA  length = 110
FEATURE                Location/Qualifiers
REGION                 1..110
                       note = CD38-Targeting Moiety
source                 1..110
                       mol_type = protein
                       organism = synthetic construct
SEQUENCE: 65
QSVLTQPPSA SGTPGQRVTI SCSGSSSNIG NSYVSWYQQL PGTAPKLLIY RNNQRPSGVP     60
DRFSGSKSGT SASLAISGLR SEDEADYYCS AWDDNLSVLF GGGTKLTVLG              110

SEQ ID NO: 66          moltype = AA  length = 8
FEATURE                Location/Qualifiers
REGION                 1..8
                       note = CD38-Targeting Moiety
source                 1..8
                       mol_type = protein
                       organism = synthetic construct
SEQUENCE: 66
SSNIGNSY                                                              8

SEQ ID NO: 67          moltype =    length =
SEQUENCE: 67
000

SEQ ID NO: 68          moltype = AA  length = 9
FEATURE                Location/Qualifiers
REGION                 1..9
                       note = CD38-Targeting Moiety
source                 1..9
                       mol_type = protein
                       organism = synthetic construct
SEQUENCE: 68
SAWDDNLSV                                                             9
```

The invention claimed is:

1. A composition comprising an anti-CD38-antigen binding domain that comprises a variable heavy domain (VH) comprising the sequence of SEQ ID NO: 9 and a variable light domain (VL) comprising the sequence of SEQ ID NO:13.

2. A composition comprising an anti-CD38-antigen binding domain that comprises a VH comprising the sequence of SEQ ID NO:17 and a VL comprising the sequence of SEQ ID NO:21.

3. A composition comprising an anti-CD38-antigen binding domain that comprises a VH comprising the sequence of SEQ ID NO: 53 and a VL comprising the sequence of SEQ ID NO: 57.

4. The composition according to claim 1, wherein said VH and said VL are in a single polypeptide.

5. The composition according to claim 4 wherein, said polypeptide comprises a scFv linker and said polypeptide has the orientation from N- to C-terminal of VL-scFv linker-VH.

6. A composition according to claim 1, wherein said composition is an antibody comprising:

a) a heavy chain comprising said VH; and
b) a light chain comprising said VL.

7. The composition according to claim 6, wherein said heavy chain comprises said variable heavy domain and a heavy constant domain selected from the group consisting of the heavy constant domains of human IgG1, IgG2 and IgG4, or variants thereof.

8. The composition according to claim 7, wherein said heavy constant domain is the heavy constant domain of human IgG1.

9. The composition according to claim 8, wherein said heavy constant domain is a variant of the heavy constant domain of human IgG1.

10. The composition according to claim 9, wherein said variant heavy constant domain of human IgG1 has ablated FcγR binding.

11. A nucleic acid composition encoding said composition according to claim 7, wherein said nucleic acid composition comprises:

a) a first nucleic acid encoding said first polypeptide; and
b) a second nucleic acid encoding said second polypeptide.

12. A nucleic acid composition comprising a nucleic acid encoding said composition according to claim 4.

13. An expression vector composition comprising said nucleic acid of claim 12.

14. An expression vector composition comprising said first and second nucleic acids of claim 11.

15. An expression vector composition comprising:
 a) a first expression vector comprising said first nucleic acid of claim 11; and
 b) a second expression vector comprising said second nucleic acid of claim 11.

16. A host cell comprising said expression vector composition according to claim 13.

17. A method of making a composition comprising an anti-CD38 antigen binding domain, comprising culturing said host cell of claim 16 under conditions wherein said composition comprising the anti-CD38 binding domain is expressed, and recovering said composition.

18. A method of treating multiple myeloma comprising administering to a subject in need thereof an effective amount of said composition according to claim 1.

19. A method of treating multiple myeloma comprising administering to a subject in need thereof an effective amount of said composition according to claim 2.

20. A method of treating multiple myeloma comprising administering to a subject in need thereof an effective amount of said composition according to claim 3.

* * * * *